``

US008580776B2

(12) United States Patent
Feinstein et al.

(10) Patent No.: US 8,580,776 B2
(45) Date of Patent: Nov. 12, 2013

(54) COMPOSITIONS AND METHODS FOR TREATING NEURODEGENERATING DISEASES

(75) Inventors: Douglas L. Feinstein, Chicago, IL (US); Maria Vittoria Simonini, New Haven, CT (US); Sergey Kalinin, Chicago, IL (US); Paul E. Polak, Munster, IN (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 158 days.

(21) Appl. No.: 12/906,914

(22) Filed: Oct. 18, 2010

(65) Prior Publication Data

US 2011/0086845 A1    Apr. 14, 2011

Related U.S. Application Data

(63) Continuation-in-part of application No. 12/171,172, filed on Jul. 10, 2008.

(60) Provisional application No. 61/279,098, filed on Oct. 16, 2009, provisional application No. 61/279,104, filed on Oct. 16, 2009, provisional application No. 61/331,229, filed on May 4, 2010, provisional application No. 61/361,745, filed on Jul. 6, 2010, provisional application No. 60/948,811, filed on Jul. 10, 2007.

(51) Int. Cl.
*A61K 31/55* (2006.01)
*A61K 31/198* (2006.01)
*A61K 31/5375* (2006.01)
*A61P 25/28* (2006.01)
*A61P 25/16* (2006.01)

(52) U.S. Cl.
USPC .......... 514/183; 514/217; 514/567; 514/239.2

(58) Field of Classification Search
USPC .................................. 514/217, 564, 567, 182
See application file for complete search history.

(56) References Cited

U.S. PATENT DOCUMENTS

| | | | |
|---|---|---|---|
| 4,497,826 | A | 2/1985 | Narabayashi et al. |
| 4,690,949 | A | 9/1987 | Yoshida et al. |
| 6,228,875 | B1 | 5/2001 | Tsai et al. |
| 6,403,645 | B2 | 6/2002 | Schildkraut et al. |
| 6,610,725 | B1 | 8/2003 | Imbert et al. |
| 2002/0111384 | A1* | 8/2002 | Boudrie et al. ............... 514/567 |
| 2003/0077227 | A1 | 4/2003 | Dugger |
| 2005/0009925 | A1 | 1/2005 | Bymaster et al. |
| 2005/0096327 | A1 | 5/2005 | Caprathe et al. |
| 2006/0105394 | A1 | 5/2006 | Pomara |
| 2006/0128705 | A1 | 6/2006 | Wong et al. |
| 2007/0010517 | A1 | 1/2007 | Airoldi et al. |
| 2007/0083046 | A1 | 4/2007 | Campbell et al. |
| 2008/0026081 | A1 | 1/2008 | Unterbeck et al. |

FOREIGN PATENT DOCUMENTS

| | | |
|---|---|---|
| WO | 02/053104 | 7/2002 |
| WO | WO 2007/005962 A2 * | 7/2005 |
| WO | WO 2007/109851 A1 * | 3/2006 |

OTHER PUBLICATIONS

PubMed—Causes-brain tumor—http://www.ncbi.nlm.nih.gov/pubmedhealth/PMH0004485/[Jul. 20, 2012 7:24:49 AM] Causes, Incidence and Risk Factors,pp. 6, Dec. 1, 2011) see p. 1.*
(Alzheimer's disease: Causes—www.MayoClinic.comhttp://www.mayoclinic.com/health/alzheimersdisease/DS00161/DSECTION=causes[Jul. 20, 2012 2:32:03 PM] Causes by Mayo Clinic Staff,pp. 2, Jan. 18, 2011) see p. 1.*
Birthelmer et al., "Neurotransmitter release and its presynaptic modulation in the rat hippocampus after selective damage to cholinergic or/and serotonergic afferents", Brain Research Bulletin, vol. 59 No. 5 pp. 371-381, 2003.
Buoso et al., "β-Amyloid precursor protein metabolism: focus on the functions and degradation of its intracellular domain", Pharmacological Research 62 (2010) pp. 308-317.
Dyon-Laurent et al., "Noradrenergic hyperactivity in hippocampus after partial denervation: pharmacological, behavioral, and electrophysiological studies", Exp Brain Research (1994) 99: 259-266.
Goedert, "Neuronal localization of amyloid beta protein precursor mRNA in normal human brain and in Alzheimer's disease", The EMBO Journal vol. 6 No. 12 pp. 3627-3632, 1987.
Prehn-Kristensen et al., "Methylphenidate does not improve interference control during a working memory task in young patients with attention-deficit hyperactivity disorder", Brain Research 1388 (2011) pp. 56-68.
Bartzokis G., (2004) "Review: Age-related myelin breakdown: a developmental model of cognitive decline and Alzheimer's disease." Neurobiol Aging Jan; 25(1): 5-18; author reply 49-62.
Bartzokis G. (2009). "Alzheimer's disease as homeostatic responses to age-related myelin breakdown" Neurobiol Aging. Sep. 21, 2009, pp. 1-31.
Budde et al., 2008, "Axonal injury detected by in vivo deffusion tensor imaging correlates with neurological disability in a mouse model of multiple sclerosis," NMR Biomed. 21: 589-597.
Dziedzic et al., 2010, "Wallerian Degeneration: A Major Component of Early Axonal Pathology in Multiple Sclerosis", Brain Pathol. 20: 976-985.
German et al., 1988, "The human locus coeruleus: computer reconstruction of cellular distribution," J. Neurosci. 8: 1776-1788.
Gilgun-Sherki et al., 2003, "Riluzole suppresses experimental autoimmune encephalomyelitis: implications for the treatment of multiple sclerosis," Brain Res. 989: 196-204.
Helkamaa et al., 2007, "Increased catechol-O-methyltransferase activity and protein expression in OX-42-positive cells in the substantia nigra after lipopolysaccharide microinfusion," Neurochem. Int. 51: 412-423.
Holstege and Bongers, 1991, "Ultrastructural aspects of the coeruleo-spinal projection," Prog. Brain Res. 88: 143-156.
Huang et al., 2005, "Activation of catechol-O-methyltransferase in astrocytes stimulates homocysteine synthesis and export to neurons," Glia 51: 47-55.

(Continued)

*Primary Examiner* — Sreeni Padmanabhan
*Assistant Examiner* — Jason A Deck
(74) *Attorney, Agent, or Firm* — McDonnell Boehnen Hulbert & Berghoff LLP

(57) ABSTRACT

This invention provides agents, compositions, pharmaceutical compositions and methods for treating or slowing the progression of a neurodegenerating disease, such as Alzheimer's disease and a demyelinating disease.

10 Claims, 28 Drawing Sheets

(56) References Cited

OTHER PUBLICATIONS

Irvine and Blakemore, 2006, "Age Increases axon loss associated with primary demyelination in cuprizone-induced demyelination in C57BL/6 mice", J. Neuroimmunol. 175: 69-76.

Learish et al., 1999, "Intraventricular transplantation of oligodendrocyte progenitors into a fetal myelin mutant results in widespread formation of myelin," Ann Neurol 46: 716.

Levine et al., 2001, "The oligodendrocyte precursor cell in health and disease," Trends in Neuroscience 24: 39-37.

Lindner et al., 2009, "Chronic toxic demyelination in the central nervous system leads to axonal damage despite remyelination," Neurosci. Lett. 453: 120-125.

Lindvall & Kokaia, 2006, "Stem cells for the treatment of neurological disorders," Nature 441: 1094-1096.

Mahad et al. 2009, "Mitochondrial changes within axons in multiple sclerosis," Brain 132: 1161-1174.

Mucke et al. 2000, "High-level neuronal expression of abeta 1-42 in wild-type human amyloid protein precursor transgenic mice: synaptotxicity without plaque formation," J Neurosci 20: 4050-4058.

Muller, 2009, "Levodopa/carbidopa and entacapone in the treatment of Parkinson's disease: efficacy, safety and patient preference" Patient Prefer. Adherence 3: 51-59.

Muller et al., 1993 "Therapy with central active catechol-O-methyltransferase (COMT)-inhibitors: is addition of monoamine oxidase (MAO)-inhibitors necessary to slow progress of neurodegenerative disorders?" J. Neural Transm. Gen. 92: 187-195.

Nord et al., 2010, "The effect of peripheral enzyme inhibitors on levodopa concentrations in blood and CSF," Movement Disord. 25: 363-367.

Proudfit and Clark, 1991, "The projections of locus coeruleus neurons to the spinal cord," Prog Brain Res., 88: 123-141.

Sharp & Keirstead, 2007, "Therapeutic applications of oligodendrocyte precursors derived from human embryonic stem cells," Curr Opin Biotechnol. 18: 434-440.

Szot et al., 2009, "Age-dependent changes in noradrenergic locus coeruleus system in wild-type and APP23 transgenic mice," Neurosci. Lett. 463: 93-97.

Tanaka et al., 1997, "Development regulation of spinal motoneurons by monaminergic nerve fibers," J. Peripher. Nerv. Syst. 2: 323-332.

Trojanowski et al., 1986, "An immunocytochemical study of normal and abnormal human cerebrospinal fluid with monoclonal antibodies to glial fibrillary acidic protein," Acta Cytol. 30: 235-239.

Verhagen-Kamerbeek et al., 1993, "Attenuation of haloperidol-induced catelepsy by noradrenaline and L-threo-DOPS," J. Neural Transm. Park Dis. Dement. 6: 17-26.

Whittemore et al., 1993, "Concurrent isolation and characterization of oligodendrocytes, microglia and astrocytes from adult human spinal cord," Int J Dev Neurosci. 11(6): 755-764.

Caccamo et al., "Molecular Interplay between Mammalian Target of Rapamycin (mTOR), Amyloid-β, and Tau", The Journal of Biological Chemistry vol. 285, No. 17, pp. 13107-13120, Apr. 23, 2010.

Gosain et al., "Norepinephrine-Mediated Suppression of Phagocytosis by Wound Neutrophils", Journal of Surgical Research 152, 311-318, 2009.

Götz et al., "Dissecting Toxicity of Tau and β-Amyloid", Biology of Neurodegeneration, 7; 10-12, Feb. 13, 2010.

Heneka et al., "Locus Ceruleus Controls Alzheimer's Disease Pathology by Modulating Microglial Functions Through Norepinephrine", PNAS, vol. 107, No. 13, Mar. 30, 2010 pp. 6058-6063.

Hoogendijk et al., "Increased Activity of Surviving Locus Ceruleus Neurons in Alzheimer's Disease", American Neurological Association, 1999, 45:82-91.

Jenner et al., "Noradrenaline and 5-Hydroxytryptamine Modulation of Brain Dopamine Function: Implications for the Treatment of Parkinson's Disease", Br. J. Clin. Pharmac. (1983) 15, 277S-289S.

Johnson et al., "Levodopa in Senile Dementia", British Medical Journal, Jun. 17, 1978, p. 1625.

Kalinin et al., "Noradrenaline Deficiency in Brain Increases β-Amyloid Plaque Burden in an Animal Model of Alzheimer's Disease", Neurobiology of Aging 28 (2007); pp. 1206-1214.

Koestner et al., "Animal Model of Human Disease", American Journal of Pathology, vol. 78, No. 2, Feb. 1975, pp. 361-364.

Kong et al., "Norepinephrine Promotes Microglia to Uptake and Degrade Amyloid β Peptide through Upregulation of Mouse Formyl Peptide Receptor 2 and Induction of Insulin-Degrading Enzyme", The Journal of Neuroscience, Sep. 1, 2010-30(35); pp. 11848-11857.

Lacoste et al., "Noradrenaline Modulates Oyster Hemocyte Phagocytosis via a β-Adrenergic Receptor—cAMP Signaling Pathway", General and Comparative Endocrinology 122, pp. 252-259 (2001).

Ortega et al., "Norepinephrine as Mediator in the Stimulation of Phagocytosis Induced by Moderate Exercise", Eur J. Appl. Physiol (2005) 93: 714-718.

Peskind et al., "Effects of Alzheimer's Disease and Normal Aging on Cerebrospinal Fluid Norepinephrine Responses to Yohimbine and Clonidine", Arch Gen Psychiatry, vol. 52, Sep. 1995, pp. 774-782.

Peskind et al., "Oral Physostigmine in Alzheimer's Disease: Effects on Norepinephrine and Vasopressin in Cerebrospinal Fluid and Plasma", Society of Biological Psychiatry (1995), 38:pp. 532-538.

Simonini et al., "Increasing CNS Noradrenaline Reduces EAE Severity", J. Neuroimmune Pharmacol, Dec. 4, 2009.

Steininger et al., "Beta-adrenergic Stimulation Suppresses Phagocytosis via Epac Activation in Murine Microglial Cells", J. Brain Research 2011, pp. 1-12.

Tobinick et al., "Rapid Cognitive Improvement in Alzheimer's Disease Following Perispinal Etanercept Administration", Journal of Neuroinflammation, 2008, 5:2; pp. 1-10.

vanEersel et al., "Sodium Selenate Mitigates Tau Pathology, Neurodegeneration, and Functional Deficits in Alzheimer's Disease Models", PNAS, Aug. 3, 2010, vol. 107, No. 31, pp. 13888-13893.

Bayer et al., "Key Factors in Alzheimer's Disease: β-amyloid Precursor Protein Processing, Metabolism and Intraneuronal Transport", Brain Pathology, 2001, 11: 1-11.

Bonda et al., "Oxidative stress in Alzheimer disease: A possibility for prevention", Neuropharmacology, 2010, pp. 1-5.

Mita et al., "Widespread Expression of Amyloid Beta-Protein Precursor Gene in Rat Brain", American Journal of Pathology, vol. 134, No. 6, Jun. 1989, pp. 1253-1261.

Sara et al., "Noradrenergic hyperactivity after partial fornix section: role in cholinergic dependent memory performance", Experimental Brain Research, 1992, 89: pp. 125-132.

Sisodia et al., "Evidence That β-Amyloid Protein in Alzheimer's Disease Is Not Derived by Normal Processing", Science, vol. 248, pp. 492-495, Apr. 27, 1990.

Buxbaum, et al., Proc. Natl. Acad. Sci. USA, vol. 89, pp. 10075-10078; Nov. 1992.

Heneka, et al., The Journal of Neuroscience, vol. 22, No. 7, pp. 2434-2442; 2002.

Caccamo, et al., Neurobiology of Aging, vol. 26, pp. 645-654; 2005.

Goldstein, Dihydroxyphenylserine (L-DOPS): A norepinephrine prodrug, Cardiovascular Drug Reviews, 24:189-203.

Hardy, et al., Trends in Pharmacological Sciences, vol. 12, Abstrtact; 1991.

Herrmann, et al., The Journal of Neuropsychiatry and Clinical Neurosciences, vol. 16, pp. 261-176; 2004.

Madrigal, et al., (2006) "Effects of Noradrenaline on Neuronal NOS2 Expression and Viability", Antioxidant & Redox Signaling, 8(5-6):885-92.

Madrigal, et al., (2005) "Norepinephrine protects cortical neurons against microglial-induced cell death," J. Neurosci. Research, 81(3):390-6.

Warner (Retrieved on Nov. 20, 2010 from the Internet: <URL: http://222.webmd.com/alzheimers/news/20030729/antidepressant-alzheimers).

Camacho, et al., Psychopharmacology, 1996, 124:347-354.

Peskind, et al., Alzheimer Dis Assoc. Disord., 1995, 19:23-28.

Giladi, 2008, Movement Disorders, vol. 23, Suppl. 2, pp. S482-S488.

Mohs, et al., "Atomoxetine Augmentation of Cholinesterase Inhibitor Therapy in Patients with Alzheimer Disease: 6-Month, Randomized, Double-blind, Placebo-Controlled, Parallel-Trial Study," Am. J. Geriatr. Psychiatry, 2009, 17:752-59.

Candore, et al., rejuvenation Res., 2010, 13:301-313.

(56) References Cited

OTHER PUBLICATIONS

Ittner, et al., "Dendritic function of tau mediates amyloid-B toxicity in Alzhemer's disease mouse models," Cell, 2010, pp. 387-397.
Weil-Malherbe, et al., "The uptake of circulating [3H]norepinephrine by the pituitary gland and various areas of the brain," J. Neurochemistry, 1961, 8:55-64.
Blanchard, et al., "Pharmacologic reversal of neurogenic and neuroplastic abnormalities and cognitive impairments without affecting AB and tau pathologies in 3xTg-AD mice," Acta Neuropathol., available on line Aug. 10, 2010.
The Merck Manual reference ([Retrieved online on Apr. 29, 2009] Retrieved from the Internet: <URL:http://www.merck.com/mmhe/sec06/ch083/ch083c.html).
Office Action for U.S. Appl. No. 12/171,172 mailed on Jul. 24, 2012.
Office Action for U.S. Appl. No. 12/171,172 mailed on Aug. 26, 2011.
Office Action for U.S. Appl. No. 12/171,172 mailed on Dec. 28, 2010.
Office Action for U.S. Appl. No. 12/171,172 mailed on Apr. 14, 2010.

* cited by examiner

A.        B.

A

B

SEQUENCE LISTING

```
<160> NUMBER OF SEQ ID NOS: 19

<210> SEQ ID NO 1
<211> LENGTH: 21
<212> TYPE: DNA
<213> ORGANISM: Artificial
<220> FEATURE:
<223> OTHER INFORMATION: Synthetic

<400> SEQUENCE: 1
ggtgagtttg taagtgatgc c                                          21

<210> SEQ ID NO 2
<211> LENGTH: 20
<212> TYPE: DNA
<213> ORGANISM: Artificial
<220> FEATURE:
<223> OTHER INFORMATION: Synthetic

<400> SEQUENCE: 2
tcttcttctt ccacctcagc                                            20

<210> SEQ ID NO 3
<211> LENGTH: 21
<212> TYPE: DNA
<213> ORGANISM: Artificial
<220> FEATURE:
<223> OTHER INFORMATION: Synthetic

<400> SEQUENCE: 3
ccctcgccat ggtaaataca t                                          21

<210> SEQ ID NO 4
<211> LENGTH: 21
<212> TYPE: DNA
<213> ORGANISM: Artificial
<220> FEATURE:
<223> OTHER INFORMATION: Synthetic

<400> SEQUENCE: 4
actggatggt acgcttggtc t                                          21

<210> SEQ ID NO 5
<211> LENGTH: 21
<212> TYPE: DNA
<213> ORGANISM: Artificial
```

```
<220> FEATURE:
<223> OTHER INFORMATION: Synthetic

<400> SEQUENCE: 5
cctgaagtac cccattgaac a                                              21

<210> SEQ ID NO 6
<211> LENGTH: 21
<212> TYPE: DNA
<213> ORGANISM: Artificial
<220> FEATURE:
<223> OTHER INFORMATION: Synthetic

<400> SEQUENCE: 6
cacacgcagc tcattgtaga a                                              21

<210> SEQ ID NO 7
<211> LENGTH: 24
<212> TYPE: DNA
<213> ORGANISM: Artificial
<220> FEATURE:
<223> OTHER INFORMATION: Synthetic

<400> SEQUENCE: 7
gccaagtatg atgacatcaa gaag                                           24

<210> SEQ ID NO 8
<211> LENGTH: 24
<212> TYPE: DNA
<213> ORGANISM: Artificial
<220> FEATURE:
<223> OTHER INFORMATION: Synthetic

<400> SEQUENCE: 8
tccaggggtt tcttactcct tgga                                           24

<210> SEQ ID NO 9
<211> LENGTH: 21
<212> TYPE: DNA
<213> ORGANISM: Artificial
<220> FEATURE:
<223> OTHER INFORMATION: Synthetic

<400> SEQUENCE: 9
tgcactatta tcccctaaat g                                              21

<210> SEQ ID NO 10
<211> LENGTH: 21
<212> TYPE: DNA
<213> ORGANISM: Artificial
<220> FEATURE:
<223> OTHER INFORMATION: Synthetic

<400> SEQUENCE: 10
tgtctatcaa gtcgggtcta a                                              21

<210> SEQ ID NO 11
<211> LENGTH: 21
<212> TYPE: DNA
<213> ORGANISM: Artificial
<220> FEATURE:
<223> OTHER INFORMATION: Synthetic

<400> SEQUENCE: 11
gtaagcagcc tcagccgaaa c                                              21
```

```
<210> SEQ ID NO 12
<211> LENGTH: 21
<212> TYPE: DNA
<213> ORGANISM: Artificial
<220> FEATURE:
<223> OTHER INFORMATION: Synthetic

<400> SEQUENCE: 12
ccacataaag cctcccccaca g                                              21

<210> SEQ ID NO 13
<211> LENGTH: 22
<212> TYPE: DNA
<213> ORGANISM: Artificial
<220> FEATURE:
<223> OTHER INFORMATION: Synthetic

<400> SEQUENCE: 13
gcctggccag tgtagcagtc tt                                              22

<210> SEQ ID NO 14
<211> LENGTH: 22
<212> TYPE: DNA
<213> ORGANISM: Artificial
<220> FEATURE:
<223> OTHER INFORMATION: Synthetic

<400> SEQUENCE: 14
cagcacccaa actcaccaag tg                                              22

<210> SEQ ID NO 15
<211> LENGTH: 21
<212> TYPE: DNA
<213> ORGANISM: Artificial
<220> FEATURE:
<223> OTHER INFORMATION: Synthetic

<400> SEQUENCE: 15
gggcttctct gaccaggtgt a                                               21

<210> SEQ ID NO 16
<211> LENGTH: 20
<212> TYPE: DNA
<213> ORGANISM: Artificial
<220> FEATURE:
<223> OTHER INFORMATION: Synthetic

<400> SEQUENCE: 16
ggcaggcatg ggtagcatag                                                 20

<210> SEQ ID NO 17
<211> LENGTH: 21
<212> TYPE: DNA
<213> ORGANISM: Artificial
<220> FEATURE:
<223> OTHER INFORMATION: Synthetic

<400> SEQUENCE: 17
ctgtcacgga gatcaatgtg g                                               21

<210> SEQ ID NO 18
<211> LENGTH: 21
<212> TYPE: DNA
<213> ORGANISM: Artificial
<220> FEATURE:
<223> OTHER INFORMATION: Synthetic

<400> SEQUENCE: 18
```

```
aaggcgtagc tgaacaaggt g                                              21

<210> SEQ ID NO 19
<211> LENGTH: 21
<212> TYPE: PRT
<213> ORGANISM: Artificial
<220> FEATURE:
<223> OTHER INFORMATION: Synthetic

<400> SEQUENCE: 19

Met Glu Val Gly Trp Tyr Arg Ser Pro Phe Ser Arg Val Val His Leu
1               5                   10                  15

Tyr Arg Asn Gly Lys
            20
```

COMPOSITIONS AND METHODS FOR TREATING NEURODEGENERATING DISEASES

This application is a continuation-in-part of U.S. patent application Ser. No. 12/171,172, filed Jul. 10, 2008 which claims the benefit of priority to U.S. provisional application Ser. No. 60/948,811, filed Jul. 10, 2007. This application also relates to and claims the benefit of priority to provisional application Ser. Nos. 61/279,098, filed Oct. 16, 2009, 61/279,104, filed Oct. 16, 2009, 61/331,229, filed May 4, 2010, and 61/361,745, filed Jul. 6, 2010, The disclosures of each of the above applications are incorporated herein by reference in their entireties.

The invention was made with government support under grant numbers NS44945 and NS31556 awarded by the National Institute of Health and VA MERIT grant number AR-M355U_20100826_104754. The government has certain rights in the invention.

BACKGROUND OF THE INVENTION

1. Field of the Invention

The application relates to the field of neurobiology. In particular, the application relates to agents, compositions and methods useful for neuroprotection, specifically, for preventing, slowing the progression or onset of, or reducing the risks of a central nervous system disease in a patient, particularly a demyelinating disease.

2. Description of Related Art

Alzheimer's disease (AD) is a neurodegenerative disease of the central nervous system (CNS) that usually affects people over 65 years old. Although typically presenting with symptoms in the aged, the disease can develop many years before it is diagnosed. When symptoms first appear, the patients often exhibit memory loss and, at later stages, confusion, anger, mood swings, language difficulties, long-term memory loss and a sense of withdrawal. As the disease progresses, minor and major bodily functions are lost, leading ultimately to death. The disease is associated with amyloid plaque deposits and tangles in the brain, but the cause of AD is not well understood. Currently, there is no effective treatment to stop or cure AD. Thus, a better way to prevent and manage the disease is essential.

Parkinson's disease (PD) is another neurodegenerative disorder of the CNS. PD is characterized by muscle rigidity, tremor, a slowing of physical movement, and, in severe cases, a total loss of movement. The primary symptoms of PD are caused by decreased stimulation of the motor cortex by the basal ganglia, usually a result of insufficient production and activity of dopamine produced by the dopaminergic neurons of the brain. In addition to its effects on motor function, PD is also associated with non-motor symptoms such as disorders of mood, behavior, thinking and sensations. Most PD patients are characterized as having idiopathic Parkinson's disease, i.e., having no specific identified cause. Less commonly, PD is associated with genetic lesions, toxins, head trauma, and can be drug-induced. PD is a chronic disorder that requires long-term management and care for patients. Currently, there is no cure for PD, but medication and surgery can provide temporary relief of the symptoms. Although PD is not considered a fatal disease, it may cause complications in its late stages such as choking, pneumonia and falls and can lead to death.

Multiple sclerosis (MS) is an autoimmune disease in which the immune system attacks the CNS, leading to demyelination. MS patients often suffer from a variety of symptoms, including changes in sensation, difficulties in moving, problems in speech and vision, fatigue, and acute or chronic pain. In MS patients, the immune system attacks oligodendrocytes, destroying the myelin sheath and affecting neural signal transmission in the white matter of the CNS. MS patients may suffer from relapsing forms or progressive forms of symptoms. In patients experiencing relapses, symptoms may disappear completely between episodes, but permanent neurological problems persist, especially as the disease advances. Although the cause of MS is not well understood, environmental factors can play a role, and genetic factors may determine the susceptibility of an individual to MS. Like the other neurodegenerative diseases AD and PD, currently there is no cure for MS.

In addition to MS, there are a number of other demyelinating diseases that are characterized by damage to myelin in the CNS. There are at least two types of demyelinating diseases, acquired and hereditary neurodegenerative disorders. The causes of these diseases are different, but the outcome is the same: loss of vision, hearing, ability to walk or speak and other life-altering changes. Further, dysmyelinating diseases (where myelin sheath is present but defective) may show similar symptoms. Because of the multi-faceted etymologies of diseases resulting from damaged or non-functional myelin in the CNS, they are difficult to diagnose and often impossible to cure.

Because these chronic neurodegenerative diseases are refractory to treatment, neuroprotection is an important component of disease management. For example, ibuprofen is a widely used non-steroid anti-inflammatory drug (NSAID) for relief of a variety of inflammatory symptoms. Ibuprofen has been used as a treatment of AD; however, the gastrointestinal side-effects associated with Ibuprofen has limited its suitability for daily administration to patients with neurodegenerative disease. Thus, there exists a need for better and more effective treatments resulting in neuroprotection in patients suffering from or susceptible to neurodegenerative diseases.

SUMMARY OF THE INVENTION

This invention provides biologically-active agents, compositions, and pharmaceutical compositions and methods for prophylactic and therapeutic treatment in a patient of a central nervous system (CNS) disease. Specifically, the invention provides methods for preventing and slowing the progression of a CNS disease by administering to a patient an agent that increases the levels of noradrenaline (NA) in the CNS.

In accordance with the invention, methods are provided for promoting myelination in a patient's CNS, said method comprising administering to a patient in need thereof a therapeutically effective amount of an agent that increases noradrenaline levels in the patient's CNS. In certain particular embodiments, the agent is a noradrenaline precursor. In certain other embodiments the agent further comprises at least one of an L-aromatic-amino-acid decarboxylase (LAAAD) inhibitor, a catechol O-methyl transferase (COMT) inhibitor, and a noradrenaline reuptake inhibitor. In certain other embodiments the agent further comprises at least two of an L-aromatic-amino-acid decarboxylase (LAAAD) inhibitor, a catechol O-methyl transferase (COMT) inhibitor, and a noradrenaline reuptake inhibitor. In certain other embodiments the agent further comprises all of an L-aromatic-amino-acid decarboxylase (LAAAD) inhibitor, a catechol O-methyl transferase (COMT) inhibitor, and a noradrenaline reuptake inhibitor. In certain embodiments the agent comprises a noradrenaline precursor and an LAAAD inhibitor. In certain embodiments the agent comprises a noradrenaline precursor and a noradrenaline reuptake inhibitor. Advantageously, in certain embodiments the agent comprises a noradrenaline precursor and a COMT inhibitor. In certain other embodiments the agent comprises a noradrenaline precursor, a LAAAD inhibitor and a COMT inhibitor. In certain other embodiments the agent comprises a noradrenaline precursor, a LAAAD inhibitor, and a noradrenaline reuptake inhibitor. In certain other embodiments the agent comprises a noradrenaline precursor, a COMT inhibitor and a noradrenaline reuptake inhibitor. In certain other embodiments the agent comprises a noradrenaline precursor, a LAAAD inhibitor, a COMT inhibitor and a noradreanline reuptake inhibitor. Advantageously, increased NA levels elicit at least one neural protective effect. In certain particular embodiments, the neural protective effect is exerted by a glial cell in the CNS, wherein the neural protective effect includes without limitation reduced bone morphogenetic protein (BMP) expression, increased neurotrophic factor expression, or reduced inflammation. BDNF and GDNF are examples of neurotrophic factors that have increased expression following NA treatment. In certain embodiments the neural protective effect induces oligodendrocyte progenitor cell (OPC) maturation. In certain other embodiments the glial cell is an astrocyte. In certain embodiments the patient is suffering from a demyelinating disease including, without limitation, multiple sclerosis, ischemia, perinatal hypoxia, Alzheimer's disease, Charcot-Marie-Tooth disease, Krabbe Disease, Devic's disease, Guillain-Barre Disease, encephalitis and a brain tumor. The invention also provides pharmaceutical compositions comprising a noradrenaline precursor and at least one of an LAAAD inhibitor, a COMT inhibitor, and a noradrenaline reuptake inhibitor for promoting myelination in a patient's CNS.

In another aspect, the invention provides methods of slowing progression of a demyelinating disease in a patient, said method comprising the step of administering to a patient suffering from a demyelinating disease a therapeutically effective amount of an agent that increases noradrenaline levels in the patient's CNS. In certain embodiments, the agent comprises a noradrenaline precursor. In certain other embodiments, the agent comprises a noradrenaline precursor and at least one of an L-aromatic-amino-acid decarboxylase (LAAAD) inhibitor, a catechol O-methyl transferase (COMT) inhibitor, and a noradrenaline reuptake inhibitor. In certain other embodiments the agent further comprises at least two of an L-aromatic-amino-acid decarboxylase (LAAAD) inhibitor, a catechol O-methyl transferase (COMT) inhibitor, and a noradrenaline reuptake inhibitor. In certain other embodiments the agent further comprises all of an L-aromatic-amino-acid decarboxylase (LAAAD) inhibitor, a catechol O-methyl transferase (COMT) inhibitor, and a noradrenaline reuptake inhibitor. In certain embodiments the agent comprises a noradrenaline precursor and an LAAAD inhibitor. In certain embodiments the agent comprises a noradrenaline precursor and a noradrenaline reuptake inhibitor. Advantageously, in certain embodiments the agent comprises a noradrenaline precursor and a COMT inhibitor. In certain other embodiments the agent comprises a noradrenaline precursor, a LAAAD inhibitor and a COMT inhibitor. In certain other embodiments the agent comprises a noradrenaline precursor, a LAAAD inhibitor, and a noradrenaline reuptake inhibitor. In certain other embodiments the agent comprises a noradrenaline precursor, a COMT inhibitor and a noradrenaline reuptake inhibitor. In certain other embodiments the patient is suffering from a demyelinating disease including without limitation multiple sclerosis, ischemia, perinatal hypoxia Alzheimer's disease, Charcot-Marie-Tooth disease, Krabbe Disease, Devic's disease, Guillain-Barre Disease, encephalitis and a brain tumor. The invention also provides pharmaceutical compositions comprising a noradrenaline precursor and at least one of an LAAAD inhibitor, a COMT inhibitor, and a noradrenaline reuptake inhibitor for slowing progression of a demyelinating disease in a patient.

In certain embodiments, the agent comprises a noradrenaline precursor, preferably (−)-threo-3-(3,4-dihydroxyphenyl)-L-serine (L-DOPS). The noradrenaline precursor can be converted to noradrenaline by the enzyme such as L-aromatic-amino-acid decarboxylase (LAAAD). In certain embodiments of the inventive methods, the agent further comprises a LAAAD inhibitor to prevent peripheral conversion of the noradrenaline precursor to noradrenaline thereby minimizing and preventing side effects of excess peripheral noradrenaline. In certain particular embodiments, the LAAAD inhibitor indirectly facilitates conversion of the noradrenaline precursor to noradrenaline in the CNS by minimizing peripheral conversion of the noradrenaline precursor to noradrenaline and thus preserving the levels of the precursor in the circulation. An LAAAD inhibitor suitable for use in the inventive methods does not cross the blood-brain barrier, examples of which include without limitation carbidopa and benserazide.

In other embodiments, the agent further comprises a noradrenaline reuptake inhibitor including but not limited to desipramine, atomoxetine, reboxetine, viloxazine, maprotiline, nortriptyline, buproprion, and radafaxine, preferably atomoxetine.

In certain other embodiments, the agent further comprises a COMT inhibitor including but not limited to (2E)-2-cyano-3-(3,4-dihydroxy-5-nitrophenyl)-N,N-diethylprop-2-enamide(entacapone), 3,4-dinitrocatechol (DNC) or 3-methoxy-L-tyrosine (3MT), preferably entacaptone. In yet other embodiments, the agent comprises a noradrenaline precursor and at least one of a LAAAD inhibitor, a noradrenaline reuptake inhibitor and a COMT inhibitor. Advantageously, the agent comprises a noradrenaline precursor, and further comprises at least two, or all, of a LAAAD inhibitor, a noradrenaline reuptake inhibitor and a COMT inhibitor. In certain embodiments the agent comprises a noradrenaline precursor and an LAAAD inhibitor. In certain embodiments the agent comprises a noradrenaline precursor and a noradrenaline reuptake inhibitor. Advantageously, in certain embodiments the agent comprises a noradrenaline precursor and a COMT inhibitor. In certain other embodiments the agent comprises a noradrenaline precursor, a LAAAD inhibitor and a COMT inhibitor. In certain other embodiments the agent comprises a noradrenaline precursor, a LAAAD inhibitor, and a noradrenaline reuptake inhibitor. In certain other embodiments the agent comprises a noradrenaline precursor, a COMT inhibitor and a noradrenaline reuptake inhibitor. These embodiments are suitable for use in every aspect of the invention described herein.

In yet another aspect, the invention provides methods of slowing the progression of Alzheimer's disease or multiple sclerosis in a patient, said methods comprising the step of administering to a patient suffering from Alzheimer's disease or multiple sclerosis an agent that increases noradrenaline levels in the patient's CNS, wherein the agent comprises a COMT inhibitor and a noradrenaline precursor. In certain embodiments, the agent further comprises a noradrenaline reuptake inhibitor. In certain other embodiments, the agent further comprises an LAAAD inhibitor. In yet other embodiments, the agent further comprises an LAAAD inhibitor and a noradrenaline reuptake inhibitor.

In another aspect, the invention provides methods of promoting oligodendrocyte progenitor cell maturation or survival comprising administering to a patient in need thereof an agent that increases noradrenaline levels in the patient's CNS, wherein the increased noradrenaline levels promote oligodendrocyte progenitor cell maturation. In certain embodiments, the agent is a noradrenaline precursor. In certain embodiments the agent is a noradrenaline precursor and at least one of an L-aromatic-amino-acid decarboxylase (LAAAD) inhibitor, a catechol O-methyl transferase (COMT) inhibitor, and a noradrenaline reuptake inhibitor. In certain other embodiments the agent further comprises at least two of an L-aromatic-amino-acid decarboxylase (LAAAD) inhibitor, a catechol O-methyl transferase (COMT) inhibitor, and a noradrenaline reuptake inhibitor. In certain other embodiments the agent further comprises all of an L-aromatic-amino-acid decarboxylase (LAAAD) inhibitor, a catechol O-methyl transferase (COMT) inhibitor, and a noradrenaline reuptake inhibitor. In certain embodiments the agent comprises a noradrenaline precursor and an LAAAD inhibitor. In certain embodiments the agent comprises a noradrenaline precursor and a noradrenaline reuptake inhibitor. Advantageously, in certain embodiments the agent comprises a noradrenaline precursor and a COMT inhibitor. In certain other embodiments the agent comprises a noradrenaline precursor, a LAAAD inhibitor and a COMT inhibitor. In certain other embodiments the agent comprises a noradrenaline precursor, a LAAAD inhibitor, and a noradrenaline reuptake inhibitor. In certain other embodiments the agent comprises a noradrenaline precursor, a COMT inhibitor and a noradrenaline reuptake inhibitor.

In yet another aspect, the invention provides methods for promoting oligodendrocyte progenitor cell maturation or survival comprising contacting an oligodendrocyte progenitor cell with noradrenaline. In a further aspect, the invention provides an isolated oligodendrocyte progenitor cell that has been treated by contacting the isolated oligodendrocyte progenitor cell with noradrenaline. In a further embodiment, the invention provides pharmaceutical compositions comprising a plurality of isolated oligodendrocytes that has been treated by contacting the isolated oligodendrocyte progenitor cell with noradrenaline, and a pharmaceutically acceptable excipient, diluent or a carrier. In certain particular embodiments, the pharmaceutical compositions are suitable for transplanting into the CNS of a mammal in need thereof.

In yet a further aspect, the invention provides methods of promoting myelination or slowing the progression of a demyelinating disease in a patient's CNS, said method comprising administering to a patient in need thereof a therapeutically effective amount of isolated oligodendrocyte progenitor cells that have been treated by contacting the isolated oligodendrocyte progenitor cells with noradrenaline. In yet another further aspect, the invention provides methods of promoting myelination in a patient's CNS, said method comprising administering to a patient in need thereof a therapeutically effective amount of a pharmaceutical composition comprising isolated oligodendrocytes that have been treated by contacting the isolated oligodendrocyte progenitor cells with noradreanline and a pharmaceutically acceptable excipient, diluent or a carrier.

In another aspect, the invention provides pharmaceutical compositions comprising a noradrenaline precursor, an LAAAD inhibitor and a noradrenaline reuptake inhibitor. In certain embodiments, the pharmaceutical compositions of the invention are suitable for treating, or slowing the progression of, Alzheimer's disease and multiple sclerosis. The invention in this aspect also comprises methods for treating AD or MS using said pharmaceutical compositions. Disclosed herein are methods for providing benefits to AD and MS patients by noradrenaline levels in CNS. As described throughout this application, increased noradrenaline levels can facilitate clearance of amyloid beta by, inter alia, promoting phagocytosis of amyloid beta deposits and activating proteases that degrade amyloid beta deposits in the CNS. In addition, an agent that increases myelination not only indirectly benefits AD patients but can also provide a direct benefit to patients suffering from AD. AD has been shown to be associated with demyelination of the CNS. (See Bartzokis G., (2004) "Review: Age-related myelin breakdown: a developmental model of cognitive decline and Alzheimer's disease." Neurobiol Aging. January; 25(1):5-18; author reply 49-62; Bartzokis G. (2009) "Alzheimer's disease as homeostatic responses to age-related myelin breakdown" Neurobiol Aging. 2009 Sep. 21. [Epub ahead of print]). Thus, increased noradrenaline levels in the CNS can promote, inter alia, myelin gene expression and OPC maturation, which can directly and indirectly benefit the CNS of Alzheimer's patients as well as directly providing benefits to MS patients.

Specific preferred embodiments of the invention will become evident from the following more detailed description of certain preferred embodiments and the claims.

BRIEF DESCRIPTION OF THE DRAWINGS

FIGS. 1A and 1B are photomicrographs of brain sections stained using antibody to A$\beta$1-42 in vehicle (FIG. 1A) and DSP4 (FIG. 1B) treated mice. FIGS. 1C and 1D are bar graphs of the average plaque number (FIG. 1C) and % area stained (FIG. 1D). FIG. 1E shows the relative size distribution for all plaques and the insert expands the range from 1,000 to 12,000 $\mu m^2$ to show the increased number of larger-sized plaques in the DSP4 samples. FIGS. 1A-1E demonstrate that DSP4 treatment increases plaque burden. Bar size is 500 $\mu m$.

FIG. 2A are photographs of Western blot analysis of APP C-terminal fragments in vehicle and DSP4 treated mice. FIG. 2B depicts quantification of the immunostaining showing an increase in the C-terminal fragments in the DSP4 samples. *, $P<0.05$, DSP4 versus vehicle treated, n=3.

FIGS. 3A-3C are photomicrographs showing staining for the microglial marker Mac1. FIGS. 3D-3F are photomicrographs showing staining for the astrocyte marker GFAP. FIGS. 3G-3I are graphs depicting the quantitative analysis of the Mac1 and GFAP staining showing an increase in staining for both markers in the DSP4 samples. FIGS. 3A-3I demonstrate that DSP4 treatment increases glial inflammation. FC: frontal cortex, HC: hippocampus. Size bars: A, B 100 $\mu m$; D, E 200 $\mu m$. *, $P<0.05$ unpaired T-test.

FIG. 4A is a graph showing the mRNA levels of the A$\beta$ degrading enzymes neprilysin (Nep) and insulin degrading enzyme (IDE) in brain samples from vehicle and DSP4 treated mice (*, $P<0.05$, n=4). FIG. 4B is a graph showing Nep activity in vehicle and DSP4 samples (*, $P<0.05$). FIG. 4C is a graph showing the correlation of Nep activity versus the average number of amyloid plaques per section. FIG. 4D is a graph showing the effects of increasing noradrenaline concentration on Nep activity in isolated cells.

FIGS. 4A-4D demonstrate that DSP4 treatment reduces Neprilysin expression and activity. *, P<0.05 noradrenaline versus none.

FIGS. 5A-5B demonstrate that NA increases phagocytosis of Ab.

FIGS. 6A-6C demonstrate that DSP4 treatment reduces TH expression.

FIGS. 7A-7B demonstrate that DSP4 increases NOS2 expression in neurons.

FIG. 9A shows a graph depicting the effects of NA on reducing Aβ-induced neuronal damage in primary neurons. The levels of neuronal damage, using LDH release as a neuronal damage marker, were measured as a percentage of control. C: control; Aβ: primary neurons treated with Aβ; Aβ+NA: primary neurons treated Aβ and NA; and Aβ+dbcAMP: primary neurons treated with Aβ and dbcAMP. FIG. 9B shows three photomicrographs of FJ immunostaining (a neural degeneration marker) in primary neurons either untreated (C), treated with Aβ alone (Aβ), or treated with Aβ and NA (Aβ+NA). The staining intensity was quantified as a percentage of control as illustrated in the graph in FIG. 9B.

FIG. 10 demonstrates that treatment with DSP4 worsens the severity of EAE diseases.

FIG. 11A shows the daily incidence of disease for L-DOPS treated mice and vehicle mice. FIGS. 11B and 11C show daily clinical scores for treated and non-treated mice. FIGS. 11A-11C demonstrate that L-DOPS treatment prevents the worsening of clinical scores in EAE mice.

FIGS. 12A and 12B are photomicrographs of oligospheres immunostained with antibody to Myelin Basic Protein (MBP) to show that NA increases oligosphere maturation into myelinating oligodendrocytes. FIGS. 12C and 12D are graphs showing the reduction of BMP2 and BMP4 (inhibitors of oligodendrocyte maturation) mRNA levels by QPCR analysis in astrocytes due to treatment with NA.

FIGS. 13A-D are photomicrographs of oligospheres immunostained with antibody PDGFa to show that NA increases OPC maturation. FIGS. 13A and 13B show untreated OPCs immunostained with PDGFa and FIGS. 13C and 13D show OPCs treated with NA at 30 μM for 24 hours and immunostained with PDGFa. In FIGS. 13C and 13D the PDGFa staining shows that NA induces more processes and greater a number of cells than the non-treated OPCs.

FIG. 15A shows increased myelin mRNA expression in P1 OPCs due to treatment with NA. FIG. 15B shows BMP4 and BMP antagonists Noggin and Gremlin mRNA expression in P1 OPCs due to treatment with NA. *, p<0.05, , p<0.01, *, P<0.001, t test, n=3. FIG. 15C shows photomicrographs of P1 OPCs treated with 30 μM NA for 24 hours (top panel) and control (bottom panel) immuno-stained for phospho-Smad1/5/8 (Ser463/465).

FIGS. 16A and 16B demonstrate that NA treatment reduces BMP4 expression and increases BMP antagonist Noggin expression in astrocytes.

FIG. 17 demonstrates expression of NA during the course of EAE disease is altered compared to control mice.

FIG. 18A is a graph showing decreased NA levels in the LC of MS patients. Data are means±SEM of pg NA/mg wet weight; *, P<0.05 versus controls. FIGS. 18B and 18C are photomicrographs of TH staining of the LC in control and MS patients. FIG. 18D is a graph showing no significant difference in the total number of TH+ stained neurons per field of view between the control and MS tissue. FIG. 18E is a graph showing that the average cell size was significantly increased in MS patients compared to controls. FIG. 18F shows the distribution of TH+ cell sizes. Data are means±SEM, *, P<0.05 versus controls (Bonferroni post hoc), closed circle: MS, open circle: control. FIGS. 18A-18F demonstrate that the LC in MS patients undergoes stress during disease progression.

FIGS. 19A and 19B are photomicrographs of LC tissue stained with GFAP and TH. TH-staining was also shown for identification of neurons. SCD: subcoeruleus dorsal. d: dorsal, c: central, v: ventral. FIG. 19C is a graph showing the total number of stained cell bodies and processes per field of view. FIG. 19D is a graph showing the area stained (% of view). *, P<0.05 versus control (unpaired T-test). Scale bars are 200 µm. FIGS. 19A-19D demonstrate that inflammation in the LC and the SCD is increased in EAE mice compared to control mice.

FIGS. 20A and 20B show increased GFAP staining in the LC and the nearby DTg of MS (FIG. 20B) patients compared to controls (FIG. 20A). Data are means±SEM of 9 sections per brain; *, P<0.05 versus controls. Scale bars are 200 µm. FIGS. 20C and 20D are photomicrographs showing the presence of GFAP staining around TH+ stained neurons in LC (FIG. 20C) but not in the central pons (FIG. 20D). Data are means±SEM of 9 sections per brain; *, P<0.05 versus controls. Scale bars 100 µm. FIGS. 20E and 20F are graphs of quantification of staining that show a significant increase in the number of GFAP+ stained objects (cell bodies and processes) and the total area stained (% field of view) in both the LC and the DTg (dorsal tegmental nucleus) of MS samples (FIG. 20E) versus controls (FIG. 20F). Data are means±SEM of 9 sections per brain; *, P<0.05 versus controls.

FIGS. 21A and 21B show NFκB staining in control (FIG. 21A) and EAE mouse (FIG. 21B). FIGS. 21C through 21E show staining for the NFκB p65 subunit (FIG. 21C), which was often colocalized with GFAP (FIG. 21D) in astrocytes as shown in the merged image of FIG. 21E. Scale bars are 100 µm in FIGS. 21A and 21B; and 50 µm in FIGS. 21C through 21E. FIGS. 21A-21E demonstrate increased inflammation in the LC and SCD occurs in EAE mice compared to control mice.

FIGS. 23C-23E show colocalization of SMI32 (FIG. 23C) and TH+ cell bodies (FIG. 23D) in the merged image (FIG. 23E). Scale bars are 50 µm.

FIG. 24E shows there was no significant change in the total number of TH+ stained neurons per section in the EAE mice compared to the control mice. FIG. 24F shows a significant reduction of neuronal cell body in EAE (n=1276 cells counted) versus control (n=804 cells counted) (mean±SEM; *, P<0.05). FIG. 24G shows the distribution of TH+stained cell sizes, closed circle: control, open circle: EAE. Data are means±SD of distributions calculated for the 3 control and 4 EAE mice. *, P<0.05 versus control (2-way ANOVA F(15,1)=4.17; and Bonferroni post hoc). Each cell size bin includes cells having areas of that size±25 µm².

FIG. 25 demonstrates that the LC enriched genes Nr2f6 ("EAR2") and Ascl1 (Mash1) have reduced expression in EAE indicating LC damage; and levels of NGFR, NFG, and TrkB are reduced which are needed for neuronal survival, FIG. 26A shows a reduction in NA and dopamine metabolites in EAE mice. FIG. 26B shows a reduction in dopamine in EAE mice. FIG. 26C shows the ratios of metabolites in EAE mice versus control mice.

FIGS. 27A-27C** demonstrate that Atomoxetine treatment had no effect on clinical scores whereas L-DOPS treatment stabilized scores and Atomoxetine plus L-DOPS treatment reduced clinical scores.

FIG. 28 demonstrates that increased COMT during EAE disease could breakdown NA and L-DOPS in the CNS.

DETAILED DESCRIPTION OF THE INVENTION

Figure 1:
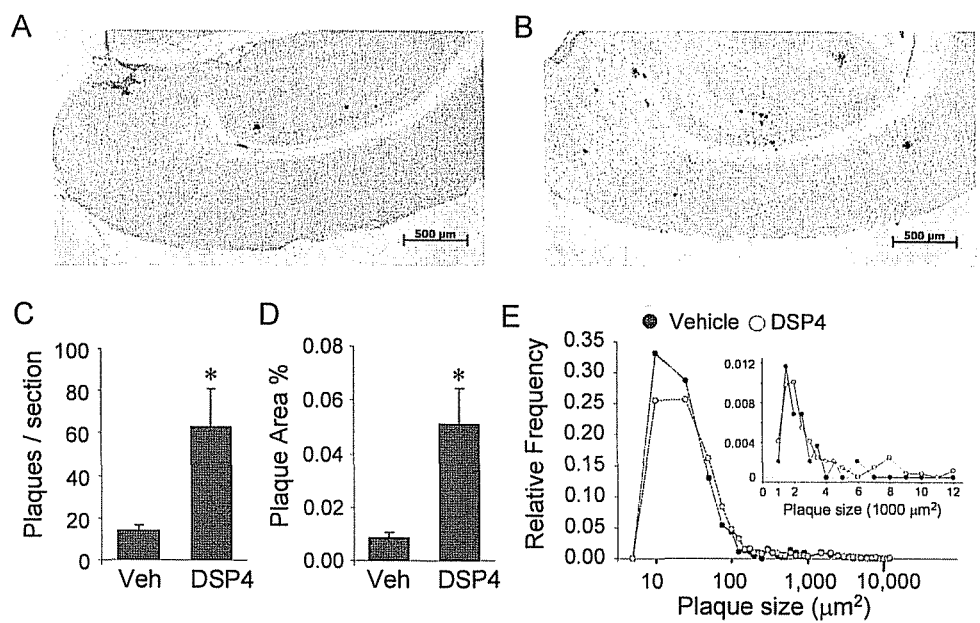
FIGS. 1A through 1E show the effect of reducing levels of brain noradrenaline by treatment with the selective noradrenergic neurotoxin N-(2-chloroethyl)-N-ethyl-2-bromobenzylamine (DSP4) on plaque number.

This invention provides neuroprotective compositions and methods of using the same. In particular, the invention provides neuroprotective methods comprising the step of administering to a patient an agent that increases the noradrenaline levels in the patient's CNS. Specifically, methods of promoting myelination in a patient's CNS, methods of slowing the progression of a demyelinating disease in a patient, methods of slowing the progression of Alzheimer's disease or multiple sclerosis in a patient and methods of promoting oligodendrocyte progenitor cell maturation or survival are provided, comprising a step of administering to a patient an agent that increases NA levels in the CNS.

There are several means by which brain NA levels can be increased in the CNS. In certain embodiments, NA levels can be increased by treatment with (−)-threo-3-(3,4-dihydroxyphenyl)-L-serine (L-DOPS, droxidopa) a synthetic catecholamino acid, which is given orally, and is converted to NA via decarboxylation by L-aromatic-amino-acid decarboxylase (LAAAD) (Goldstein, 2006, L-Dihydroxyphenylserine (L-DOPS): a norepinephrine prodrug. Cardiovasc. Drug Rev. 24, 189-203). Peripheral effects of L-DOPS can be alleviated by co-treatment with a selective LAAAD inhibitor such as carbidopa or benserazide, preferably carbidopa, that does not cross the blood brain barrier. L-DOPS has been used in rodent models of neurological disease and in dopamine-beta-hydroxylase (DBH) deficient mice to restore central NA levels.

Since conversion of L-DOPS to NA is independent of noradrenergic activity, it is expected to show effects even if brain NA levels are perturbed and reduced. Furthermore, the enzyme LAAAD is expressed in glial cells as well as neurons, therefore L-DOPS may be more efficient at increasing NA levels and promoting NA effects than noradrenaline reuptake inhibitors (NARIs) alone in glial cells, because L-DOPS can be converted by LAAAD to NA thereby increasing the overall NA levels in the CNS. The effects of L-DOPS on increasing overall NA activity in the CNS can be further augmented by co-treatment with an NARI, which increases extracellular levels of NA.

Thus, in certain embodiments, the agent used in the inventive methods comprises a noradrenaline precursor. Preferably, the NA precursor is (−)-threo-3-(3,4-dihydroxyphenyl)-L-serine (L-DOPS, droxidopa). In certain embodiments, the agent further comprises a LAAAD inhibitor that cannot penetrate the blood-brain barrier. Such an LAAAD inhibitor decreases peripheral conversion of precursor to NA and minimizes the peripheral side effects of excess NA. Suitable LAAAD inhibitors for use in the inventive methods include without limitation carbidopa and benserazide, and preferably carbidopa.

NA levels in the CNS can also be increased by use of selective or non-selective NA reuptake inhibitors (NARIs), which elevate NA levels but do not block binding of NA to α2-adrenoreceptors. NARIs are compounds that elevate the extracellular level of the neurotransmitter noradrenaline in the CNS by inhibiting its reuptake from the synaptic cleft into the presynaptic neuronal terminal. The compounds inhibit the class of neurotransmitter transporters known as norepinephrine transporters.

Antidepressant compounds are one type of NARIs. Depression is a common mood disorder in MS patients, and various anti-depressants are used for treatment, but their effects on MS symptoms have not been determined. Classical TCAs (tricylic anti-depressants such as imipramine or desipramine) block NA reuptake as well as serotonin reuptake.

In certain embodiments of the invention, the agent comprises a NARI used to increase noradrenaline levels. Selective NARIs suitable for use in the inventive methods include without limitation Reboxetine (EDRONAX®), Viloxazine (VIVALAN®), Maprotiline (DEPRILEPT®, LUDIOMIL®, PSYMION®), Nortriptyline (NORTRILEN®) and Atomoxetine (STRATTERA®, Tomoxetin). Non-selective NARIs suitable for use in the inventive methods include without limitation Amitriptyline, Amoxapine, Desipramine, Dibenzepin (NOVERIL®), Dosulepin, Doxepin, Imipramine, Iprindole, Lofepramine, Opipramol, Protriptyline, and Trimipramine. Additionally, noradrenaline- and dopamine-selective NARIs suitable for use in the inventive methods include, but are not limited to, Buproprion and Radafaxine (GSK). In certain preferred embodiments, the NARI suitable for use in the inventive methods is atomoxetine.

The enzyme COMT (catechol-O-methyl transferase) catalyzes a major pathway of catecholaminergic breakdown (Nord et al., 2010, "The effect of peripheral enzyme inhibitors on levodopa concentrations in blood and CSF," *Movement Disord.* 25: 363-367), which can reduce breakdown of the NA precursor L-DOPS as well as NA itself (Verhagen-Kamerbeek et al., 1993, "Attenuation of haloperidol-induced catalepsy by noradreanline and L-threo-DOPS," *J. Neural Transm. Park Dis. Dement.* 6: 17-26; Muller, 2009, "Levodopa/carbidopa and entacapone in the treatment of Parkinson's disease: efficacy, safety and patient preference," *Patient Prefer. Adherence* 3:51-59). This suggests that inclusion of a COMT inhibitor, as has been used for Parkinon's disease, may increase the efficacy of treatments designed to raise CNS NA levels. COMT is expressed in glial cells in the CNS (Muller et al., 1993, "Therapy with central active catechol-O-methyltransferase (COMT)-inhibitors: is addition of monoamine oxidase (MAO)-inhibitors necessary to slow progress of neurodegenerative disorders?," *J. Neural Transm. Gen.* 92:187-195; Huang et al., 2005, "Activation of catechol-O-methyltransferase in astrocytes stimulates homocysteine synthesis and export to neurons," *Glia* 51:47-55; Helkamaa et al., 2007, "Increased catechol-O-methyltransferase activity and protein expression in OX-42-positive cells in the substantia nigra after lipopolysaccharide microinfusion", *Neurochem. Int.* 51:412-423), therefore breakdown of L-DOPS or NA can occur in both the periphery as well as within the CNS. Thus, a blood-brain barrier (BBB) permeable COMT inhibitor such as 3,4-dinitrocatechol (DNC) or 3-methoxy-L-tyrosine (3MT) can reduce loss of L-DOPS and NA in the CNS. Thus, in certain advantageous embodiments, the agent comprises a noradrenaline precursor and a catechol O-methyl transferase (COMT) inhibitor. Suitable COMT inhibitors for use in the inventive methods include without limitation (2E)-2-cyano-3-(3,4-dihydroxy-5-nitrophenyl)-N,N-diethylprop-2-enamide(entacapone, COMTAN®), 3,4-dinitrocatechol (DNC) and 3-methoxy-L-tyrosine (3MT) and other COMT inhibitors that can penetrate the blood brain barrier. In certain advantageous embodiments, suitable agents used in the inventive methods for increasing noradrenaline levels in the CNS comprise a noradrenaline precursor, a NARI, a COMT inhibitor and a LAAAD inhibitor. In certain other advantageous embodiments, agents used in the inventive methods for increasing noradrenaline levels comprise a noradrenaline precursor and at least one of a NARI, a COMT inhibitor and a LAAAD inhibitor.

The compounds of the invention are administered in a therapeutically effective amount which will vary depending on a variety of factors including the activity of the specific compound employed, the metabolic stability and length of action of the compound, the age, body weight, general health, sex, diet, mode and time of administration, rate of excretion, drug combination, the severity of the particular disease-states and the patient undergoing therapy. The L-DOPS of the present invention can be administered to a patient at dosage levels in the range of about 100 to 300 mg per day orally or about 100 to 300 mg twice a day orally. The LAAAD inhibitor of the present invention can be administered to a patient at dosage levels in the range of about 70 to 100 mg per day. The reuptake inhibitor of the present invention can be administered to a patient at dosage levels in the range of about 5 to 60 mg per day orally. A combination treatment including an LAAAD inhibitor and L-DOPS of the present invention can be administered to a patient at dosage levels in the range of about 10 to 25 mg of an LAAAD inhibitor and about 100 to 250 mg of L-DOPS. A combination including an LAAAD inhibitor, L-DOPS and a COMT inhibitor of the present invention can be administered to a patient at dosage levels in the range of about 12.5 to 37.5 mg of an LAAAD inhibitor, about 50 to 150 mg of L-DOPS and about 50 to 200 mg of a COMT inhibitor.

Adult oligodendrocyte precursor or progenitor cells (OPCs) make up around 5-8% of the glial cell population in the CNS. In response to demyelination, OPCs divide and are thought to differentiate to provide new oligodendrocytes to replace those that have been lost. However, remyelination fails during the later stages of multiple sclerosis (see, Levine et al., 2001, "The oligodendrocyte precursor cell in health and disease," *Trends in Neuroscience* 24: 39-37). Thus in another aspect, the invention provides methods of promoting oligodendrocyte progenitor cell maturation or survival, said method comprising administering to a patient in need thereof an agent that increases noradrenaline levels in the patients CNS, wherein the increased noradrenaline levels promote oligodendrocyte progenitor cell maturation or survival. In certain embodiments, the agent further reduces noradrenaline reuptake in the CNS. In certain other embodiments, the agent further reduces NA degradation in the CNS.

Neural cells including OPCs have previously been used for replacing damaged or lost neural cells in a variety of CNS injury models where damages to myelin and neuronal loss have been implicated. (See, Lindvall & Kokaia, 2006, "Stem cells for the treatment of neurological disorders," *Nature* 441:1094-1096; Sharp & Keirstead, 2007, "Therapeutic applications of oligodendrocyte precursors derived from human embryonic stem cells," *Curr Opin Biotechnol.* 18:434-440). Thus, in yet a further aspect, the invention provides methods of promoting myelination in a patient's CNS, said method comprising administering to a patient in need thereof a therapeutically effective amount of isolated oligodentrocyte progenitor cells (OPCs), wherein the OPCs have been treated by contacting the cells with noradrenaline. The oligodendrocyte progenitor cells can be produced from neural stem cell culture or OPC culture. OPCs can be cultured from brain tissues from mammals of any age including adults. Thus, in certain preferred embodiments, OPCs are isolated from the tissues of a patient in need of increased myelination for autologous transplantation. Allogeneic and xenogeneic transplantations are also possible, particularly when the transplantation site is in the brain, where immunologic rejection is less severe because the immune cells are blocked by the blood-brain barrier. (See Whittemore et al., 1993, "Concurrent isolation and characterization of oligodendrocytes, microglia and astrocytes from adult human spinal cord," Int J Dev Neurosci. 11(6):755-64). It is also contemplated that OPCs can be transplanted into a patient and induced to form oligodendrocytes in vivo. Thus, OPCs may be maintained in culture using established methods, transplanted into a patient, and contacted in vivo with NA, either endogenously present in the brain or supplemented during or after surgery, to maturate into oligodendrocytes. The OPCs can for instance be introduced into the brain or spinal cord of the patient, particularly at sites where oligodendrocytes are insufficient, for example, around axons that have been demyelinated as a result of a demyelinating disease or advanced brain cancer. In humans, areas of demyelination are generally associated with plaque like structures, which can be visualized with magnetic resonance imaging (MRI). The cells may also be transplanted into other areas of the central nervous system, as glial cells are known to be able to migrate to their neural targets. A particularly useful approach is to transplant into the "mirror image" location of a target lesion in the other hemisphere, since cells are known to efficiently migrate to the corresponding location in the opposite hemisphere through the corpus collosum (Learish et al, 1999, "Intraventricular transplantation of oligodendrocyte progenitors into a fetal myelin mutant results in widespread formation of myelin," *Ann Neurol* 46:716).

The term "agent" as used herein refers to at least one compound described throughout the disclosure for use in the inventive methods to increase noradrenaline levels in the CNS of a patient.

The term "patient" as used herein refers to a mammal suffering from a neurodegenerative disease. In certain particular embodiments, the mammal is a human. In certain preferred embodiments, a patient is a human suffering from a neurodegenerative disease.

The agent for use in the inventive methods can be administered to a patient in the form of a pharmaceutical composition. Thus, in another aspect, the invention provides a composition or a pharmaceutical composition comprising a therapeutic effective amount of an agent as described herein. The cellular preparations and pharmaceutical compositions of the invention may contain formulation materials for modifying, maintaining, or preserving, in a manner that does not hinder the physiological function and viability of the agent, for example, pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobial compounds, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, betacyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; trimethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants. See REMINGTON'S PHARMACEUTICAL SCIENCES (18th Ed., A. R. Gennaro, ed., Mack Publishing Company 1990). It is within the ability of one of skill in the art to select appropriate excipients and modify the amount of amount of the excipients suitable for practice in the instant invention.

The compositions of the invention can further comprise a pharmaceutically acceptable excipient, diluent or carrier. The primary vehicle or carrier in a pharmaceutical composition may be either aqueous or non-aqueous in nature. For example, a suitable vehicle or carrier for injection may be physiological saline solution. Optimal pharmaceutical compositions can be determined by a skilled artisan depending upon, for example, the intended route of administration, delivery format, desired dosage and recipient tissue. See, e.g., REMINGTON'S PHARMACEUTICAL SCIENCES, supra. Such compositions may influence the physical state, stability, and effectiveness of the composition.

Optimal pharmaceutical compositions can be determined by one skilled in the art depending upon, for example, the intended route of administration, delivery format and desired dosage. See, for example, REMINGTON'S PHARMACEUTICAL SCIENCES, Id. Such compositions may influence the physical state, stability, rate of in vivo release and rate of in vivo clearance of the antibodies of the invention. It is within the knowledge of one of skill in the art to choose the type and adjust the amount of a pharmaceutical excipient, diluent or carrier for use in the pharmaceutical compositions provided by the invention to be used with the inventive methods described herein.

Administration routes for the pharmaceutical compositions of the invention include orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. The pharmaceutical compositions may be administered by bolus injection or continuously by infusion, or by implantation device. The pharmaceutical composition also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

The term "CNS diseases" as used herein refers to diseases that affect brain or spinal cord of the central nervous system of an patient. Exemplary CNS diseases that are suitable as targets for the inventive methods include Alzheimer's disease (AD), and demyelinating diseases including multiple sclerosis (MS). In certain embodiments, the invention provides methods for reducing a risk of developing a CNS disease, wherein neural cells are damaged in said disease, the method comprising the step of administering a therapeutically effective amount of an agent to the patient, wherein the agent increases noradrenaline levels in the patient's CNS. In certain embodiments, the patient is an aging patient especially susceptible to neurodegenerative CNS diseases. In certain embodiments, the patient is a human with a family history of neurodegenerative CNS diseases.

The term "demyelinating diseases" as used herein refers to diseases in which the myelin sheath of brain and spinal cord neurons of the central nervous system are damaged. Exemplary demyelinating diseases that are suitable targets for the inventive methods include without limitation multiple sclerosis, ischemia, perinatal hypoxia Alzheimer's disease, Charcot-Marie-Tooth disease, Krabbe Disease, Devic's disease, Guillain-Barre Disease, encephalitis and brain tumors.

The following Examples are illustrative of specific embodiments of the invention, and various uses thereof. They set forth for explanatory purposes only, and are not to be taken as limiting the invention.

EXAMPLE

Example 1

Animal Models

Transgenic APP (TgAPP) Mice

Transgenic mice (H6) overexpressing the Indiana V717F mutation of human APP under control of the PDGFR promoter (Mucke et al., 2000, "High-level neuronal expression of abeta 1-42 in wild-type human amyloid protein precursor transgenic mice: synaptotoxicity without plaque formation," *J Neurosci* 20:4050-8) were obtained from Dr. Lennart Mucke (J. David Gladstone Institute, San Francisco, Calif.). Male hemizygous H6 mice were bred to wild type C57BL6 (Charles River Breeding) females to obtain hemizygous progeny. Genotype was verified by PCR analysis of tail DNA using the forward primer 5'-GGT GAG TTT GTA AGT GAT GCC-3' (SEQ ID NO:1) and reverse primer 5'-TCT TCT TCT TCC ACC TCA GC-3' (SEQ ID NO:2). Animals were housed in groups of four under standard conditions with full access to food and water.

Lesion of the Locus Coeruleus

Hemizygous male H6 mice (aged 3 to 4 months) were injected with vehicle or with DSP4 (5 mg per kg; i.p., every two weeks) and all mice were sacrificed at age 9 months. This protocol (a low, chronic dose) results in 70% loss of LC noradrenergic neurons. Brains were dissected, the left hemispheres were fast frozen in isopentane at −30° C. and stored at −80° C. for subsequent protein and RNA studies. The right hemispheres were processed for immunohistochemistry.

Example 2

Effect of DSP4 Treatment on Amyloid Plaques

Transgenic APP (TgAPP) mice have been used extensively as a model of AD. In general, these mice exhibit some features of AD including plaque formation, cognitive dysfunction, and changes in synaptic transmission. To assess the importance of NA deficiency on amyloid deposition in an existing TgAPP mouse model of AD, the neurotoxin DSP4 (N-(2-chloroethyl)-N-ethyl-2-bromobenzylamine) was used to selectively lesion LC noradrenergic neurons. DSP4 treatment of adult rats was shown to exacerbate inflammatory responses to intracortical injection of Aβ1-42, including an increase in neuronal expression of the inducible form of nitric oxide synthase (NOS2), a localization that was observed in AD brain. The TgAPP mice harboring the V717F Indiana mutation demonstrated that chronic treatment with a lower dose of DSP4 (5 mg/kg) also increased amyloid plaque burden and levels of APP C-terminal cleavage fragments, and was paralleled by a reduction in cortical neprilysin (NEP) expression and activity. Additionally, it was shown that in primary microglial cells NA increased microglial phagocytosis of Aβ. These results suggest that LC degeneration contributes to increased amyloid deposition due to loss of noradrenergic regulation of amyloid clearance.

TgAPP H6 mice were treated with DSP4 (5 mg/kg every two weeks) beginning at age 3-4 months, and brain sections analyzed at age 9 months (FIGS. 1A-1B). Hemibrains were fixed overnight in 4% paraformaldehyde in 0.1M phosphate buffer, then overnight in 10% sucrose in 0.1M phosphate buffer, and then frozen in isopentane at −30° C. Serial sections (35 um thick) were prepared on a cryostat, and stored in cryoprotective solution (0.1M phosphate buffer: ethyleneglycol: glycerol 30:40:30) at −20° C. For Aβ1-42 staining, sections were treated with formic acid (95%, 3 min), incubated overnight at 4° C. with primary antibody directed against Aβ1-42 (1:4000 dilution, Calbiochem FCA3542 rabbit polytonal antibody raised against a synthetic peptide corresponding to amino acids 706-713 of human APP), washed, then incubated with anti-rabbit biotinylated secondary antibody (Vector BA-1000, diluted 1:400) and visualized using an ABC kit (Vector). For quantification of Aβ plaques, for each animal (n=6 vehicle treated and n=6 DSP4 treated mice) 8 stained, serial sections separated by 210 μm and spanning approximately 1.5 mm between Bregma points −1.50 mm to −3.00 mm were mounted onto glass slides and imaged with a Zeiss Axiophot 2 microscope, equipped with an Axiocam B&W MRm camera. Sections were viewed at 100× using a 10× objective, and the average plaque number and % area stained (relative to the total section area of 21 mm$^2$) per section were determined. The threshold of brightness intensity (range black=0 to white=255) used for selection of plaques was established by determining average pixel intensity from 3 areas devoid of staining, and then adjusting that value to maximize inclusion of all visibly-stained plaques while minimizing inclusion of background areas. This value was used for all sections (all stained at the same time). For all sections, visual inspection following automated counting was done to ensure exclusion of meninges, ventricular space, or other artifacts.

Representative sections from vehicle (FIG. 1A, containing 19 plaques) and DSP4 treated (B, containing 64 plaques) mice are shown in FIG. 1. Plaque burden (number and area stained) was quantified using Axiovision 4.5 Measurement Wizard software. Sections were viewed at 100× using a 10× objective, and the average plaque number (FIG. 1C) and % area stained (FIG. 1D, relative to the total section area of 21 mm$^2$) per section determined (n=8 sections per animal). The data was analyzed by two-tailed t-test assuming equal variances; *, P <0.05. The relative size distribution for all plaques detected in vehicle (n=626) and DSP4 treated (n=3009) brain sections is shown (FIG. 1E). The insert expands the range from 1,000 to 12,000 µm$^2$ to show increased number of larger-sized plaques in DSP4 samples. In DSP4 sections, 16/3009 plaques were >5,000 µm$^2$ versus 1/626 in the vehicle sections.

DSP4 treatment significantly increased the average plaque number (from 13.5±3 to 62.7±18 per section) and average area stained (from 1,810±464 µm$^2$, representing 0.008% of the total area per section; to 11,100±3,000 µm$^2$, or 0.051% total sectional area) at this time point. DSP4 treatment did not significantly alter the relative plaque size distribution although a few plaques (13 out of 3009 counted) with size greater than 7,000 µm$^2$ were detected in sections from the DSP4 treated mice (FIG. 1E). DSP4 treatment slightly increased average plaque size (from 135±18 (n=626 plaques total analyzed) to 174±8 µm$^2$ (n=3009)) primarily due to the few large-sized plaques detected (FIG. 1E insert); however, this increase was not statistically significant. Staining using Thioflavin-S revealed similar increases occurring in dense core plaques. DSP4-treatment did not induce plaque appearance in non-transgenic wild type littermates (data not shown).

Example 3

Effect of DSP4 on APP Processing

Brain extracts were prepared from vehicle and DSP4 treated mice and analyzed by Western blotting (FIG. 2A) using antibody G369 (directed against the APP C-terminus, which detects both APP holo-protein (top panel) and cleavage products of α- and β-secretase (C-terminal fragments, CTFs; bottom panel). FIG. 2B shows the quantification of immunostaining Densitometric analysis of band intensities shown in FIG. 2A for APP holoprotein and CTFs was carried out using ImageJ 1.31V software; the effect of DSP4 on band intensity is shown relative to the average staining intensity obtained for vehicle samples (which was set to 1.0).

Western Blotting

Brain tissue was homogenized in 8M urea. Total protein concentration was determined using the Bradford assay and BSA as standard. Proteins were separated on 8 or 15% SDS page gels, transferred to PVDF membrane and incubated with antibodies: anti-APP$^{645-694}$ G369 (1:4000), anti α-tubulin (T-9026, Sigma) (1:5000). Signals were detected using the ECL Kit (Amersham), band intensities calculated using Image J software (ImageJ 1.31V), and normalized to α-tubulin values.

Quantitative Real Time PCR

Total cytoplasmic RNA from tissues was isolated using TRIZOL reagent, (Invitrogen/GIBCO); aliquots were converted to cDNA using random hexamer primers, and mRNA levels were estimated by quantitative touchdown PCR (QPCR). PCR conditions were 35 cycles of denaturation at 94° C. for 10 s; annealing at 58-64° C. for 15 s; and extension at 72° C. for 20 s on a Corbett Rotorgene Real-Time PCR unit (Corbett, Australia). PCR was done using Taq DNA Polymerase (Invitrogen), and contained SYBR Green (SybrGreen1 10,000× concentrate, diluted 1:10,000; Molecular Probes, Eugene, Oreg.). Relative mRNA concentrations were calculated from the takeoff point of reactions using manufacturer's software, and were normalized to α-tubulin, β-actin, and glyceraldehyde-3-phosphate dehydrogenase (GDH). Melting curve analysis and agarose gel electrophoresis ensured production of single and corrected size products. The primers used were:

```
                                          (SEQ ID NO: 3)
α-tubulin forward, CCCTCGCCATGGTAAATACAT (SEQ ID NO: 4)
α-tubulin reverse, ACTGGATGGTACGCTTGGTCT (SEQ ID NO: 5)
β-actin forward, CCTGAAGTACCCCATTGAACA (SEQ ID NO: 6)
β-actin reverse, CACACGCAGCTCATTGTAGAA (SEQ ID NO: 7)
GDH forward, GCCAAGTATGATGACATCAAGAAG (SEQ ID NO: 8)
GDH reverse, TCCAGGGGTTTCTTACTCCTTGGA (SEQ ID NO: 9)
IDE forward, TGCACTATTATCCCCTAAATG (SEQ ID NO: 10)
IDE reverse, TGTCTATCAAGTCGGGTCTAA (SEQ ID NO: 11)
NEP forward, GTAAGCAGCCTCAGCCGAAAC (SEQ ID NO: 12)
NEP reverse, CCACATAAAGCCTCCCCACAG
```

Figure 2:
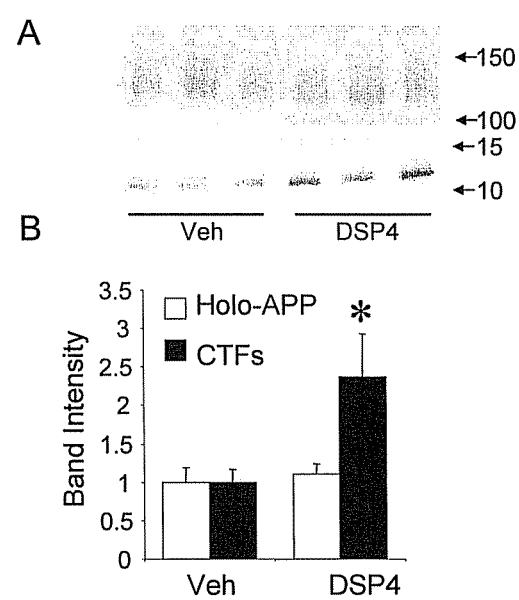
FIGS. 2A and 2B show the effect of DSP4 treatment on APP C-terminal fragments.

Western blot analysis of cortical lysates using a polyclonal antibody against APP revealed similar levels of the high molecular weight holoAPP in vehicle versus DSP4 treated TgAPP mice (FIG. 2). However, a significant increase (about 2-fold) was observed in bands migrating at 13 kDa which correspond to the APP C-terminal fragments (CTFs) produced by secretase cleavage. Thus, DSP4 treatment caused an approximately 2.5-fold increase in levels of CTFs but had no effect on levels of the holoAPP. Equal sample loading was verified using an antibody to α-tubulin (not shown). This suggested that DSP4 may cause an increase in APP processing or a decrease in CTF removal. Western blot and PCR analysis of samples prepared from the 9 month-old mice did not reveal any significant changes in BACE1, PSEN1, or Adam10 mRNA or BACE1 protein levels (data not shown), nor in human APP mRNA, suggesting that increased CTF levels were not due to increased APP processing or to effects on transgene expression.

Example 4

Effects of DSP4 on Glial Activation

Figure 3:
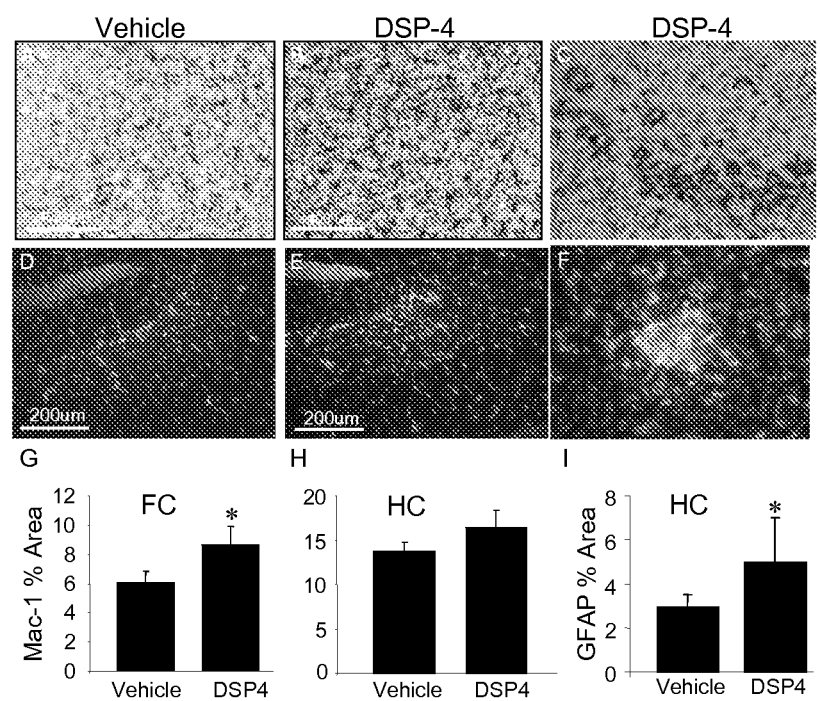
FIGS. 3A through 3I show the effects of DSP4 on glial activation.

The effects of DSP4 treatment on glial activation were assessed in hippocampus and frontal cortex by staining for microglial marker Mac1 and astrocyte marker GFAP (FIG. 3). Sections from vehicle and DSP4 treated H6 mice brains were stained with antibodies directed against Mac1 to assess microglial activation (FIG. 3A-C); and GFAP to assess astrocyte activation (FIG. 3D-F). Images in FIG. 3C and FIG. 3F show co-labeling with thioflavin-S staining to demonstrate increased glial activation surrounding amyloid plaques. FIGS. 3G-3I show quantitative analysis of Mac1 (FIG. 3G-3H) and GFAP staining (FIG. 3I).

Hemibrains were fixed overnight in 4% paraformaldehyde in 0.1M phosphate buffer, then overnight in 10% sucrose in 0.1M phosphate buffer, and then frozen in isopentane at −30° C. Serial sections (35 um thick) were prepared on a cryostat, and stored in cryoprotective solution (0.1M phosphate buffer: ethyleneglycol:glycerol 30:40:30) at −20° C. For Mac-1 staining, sections were incubated with rat anti-mouse Mac-1 (1:1000 dilution, Serotec MCA711) overnight at 4° C., washed, then incubated with biotinylated goat anti-rat AB (Serotec STAR80B. diluted 1:40) and staining visualized with ABC kit. For GFAP staining rat monoclonal anti-GFAP (2.2B10) were used at dilution 1:500, followed by anti-rat FITC labeled secondary AB (1:400 dilution) (Jackson labs). Serial sections 210 um apart were stained, mounted, and slides examined with a Zeiss Axiophot 2 microscope, equipped with Axiocam MRm camera. Staining was quantified using software provided by the manufacturer (Zeiss AxioVision). GFAP and Mac1 staining was quantified in 3 different areas on each of 4 serial sections for each animal (n=3 or 4 for Mac1; n=7 or 9 for GFAP staining) The data was average area stained per section (as % total area) from DSP4-treated (n=3 for Mac1; n=7 for GFAP) and vehicle-treated (n=4 for Mac1; n=9 for GFAP) mice. For Mac1, the data is shown for Frontal Cortex (FC) and Hippocampus (HC); for GFAP data is shown only for HC since staining in FC was low or absent.

DSP4-treatment increased Mac1 staining in both regions although only the effect measured in frontal cortex (approximately 40% increase) reach statistical significance (FIG. 3G). DSP4 treatment had little effect on the low levels of GFAP staining observed in the frontal cortex (not shown), but significantly increased GFAP staining (approximately 68%) in the hippocampus (FIG. 3I). As shown by others, strongest glial activation was observed immediately adjacent to amyloid plaques (FIG. 3C, 3F).

Example 5

Effect of DSP4 on Amyloid Degradation

Figure 4:
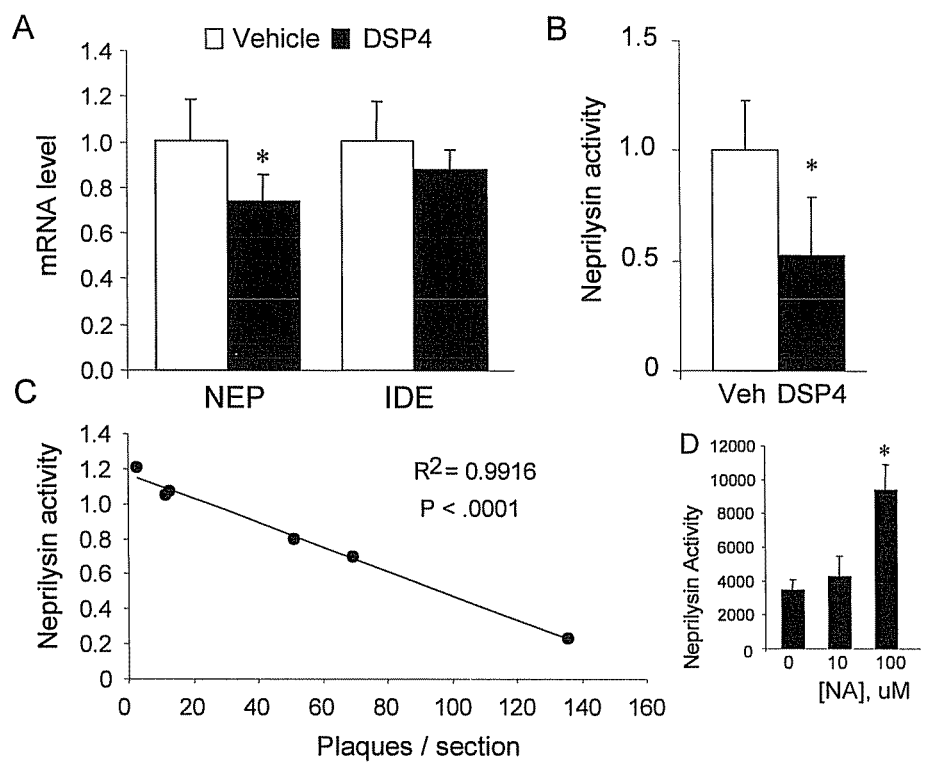
FIGS. 4A through 4D show the effect of DSP4 treatment on metallopeptidase expression.

Comparative real time RT-PCR (or quantitative PCR, QPCR) was used to measure mRNA levels of the Aβ degrading enzymes neprilysin (Nep) and insulin degrading enzyme (IDE) in brain samples from vehicle and DSP4 treated mice (FIG. 4A). Neprilysin activity in brain extracts was assayed by monitoring proteolysis of a fluorescent substrate (FIG. 4B). To assess the effects of dose, mouse neuronal N2A cells were incubated with increasing does of NA for 24 hr after which NEP activity was measured (FIG. 4D, data is mean±sd and is from n=3 samples).

Quantitative Real Time PCR

The RT-PCR condition and primers are as described in Example 3. For the RT-PCR experiment RNA levels were calculated from QPCR take off points, normalized for RNA values obtained for housekeeping genes (GDH, α-tubulin, and β-actin), and the average value for the vehicle treated RNA levels was set to 1.0. Comparisons were made using unpaired T-test, and P values <0.05 were considered to be significant.

Neprilysin Assay

Brain samples were homogenized in 9 volumes of 63 mM Tris-HCl pH 7.4 containing 1% Triton X-100, 5 μg/ml leupeptin hemisulfate salt, 5 μg/ml antipain HCl, 5 μg/ml pepstatin A; incubated for 30 min at 4° C., spun at 20,000 g for 10 min, then aliqouts of the supernatant (50 μg) were added to fluorogenic substrate N-Succinyl-Ala-Ala-Phe 7-amido 4-methylcoumarin (50 μM) for 1 hr at RT. The resulting fluorescence was measured on a GENios XFLUOR4 fluorescence plate reader using excitation of 360 nm, and emission of 485 nm. Background values were determined by incubating the lysates with Thiorphan (10 μM) or Phosphoramidon (10 μM), specific inhibitors of Neprilysin. Values are the average activities obtained for vehicle and DSP4 treated samples (n=4 each) with the average for the vehicle samples normalized to 1.0.

The levels of metallopeptidase neprilysin (NEP) mRNA were significantly reduced (approximately 20%) in cortical samples from DSP4-treated compared to samples from vehicle treated mice (FIG. 4A); in contrast only small, non-significant reductions in levels of insulin degrading enzyme (IDE, another metallopeptidase associated with amyloid degradation) were observed due to DSP4 treatment (although the lack of a significant effect may not be conclusive due to the limited sample size). The reduction in NEP mRNA levels was paralleled by an approximate 50% significant reduction in cortical NEP activity following DSP4 treatment (FIG. 4B).

A comparison of the individual values measured for NEP activity versus the average number of amyloid plaques per section measured in the same mice showed a strong negative correlation (FIG. 4C), suggesting that reductions in NEP activity are a primary factor leading to increased amyloid load. Furthermore, NA increases NEP activity in cell culture in vitro (FIG. 4D). In the results shown in FIG. 4D, mouse neuronal N2A cells were incubated with NA for 24 hr after which NEP activity was measured. Data is mean±sd and is from n=3 samples.

Example 6

Effects of NA on Microglial Phagocytosis

The ability of NA to modulate Aβ phagocytosis, another means by which amyloid plaque burden is regulated, was tested. Primary microglia were incubated with indicated concentrations of NA (FIG. 5A) or the β-AR agonist isoproterenol (FIG. 5B), in the presence of FITC-labeled Aβ1-42 (150 μM). After 4 hr, intracellular levels of Aβ were determined as described below.

Microglia Preparation

Primary murine microglial cells were generated at P1 according to standard protocols. Briefly, frontal cortices of one day old C57BL6 mice were used to prepare mixed glial cultures in T75 $cm^2$ flasks in DMEM containing 10% FCS and antibiotics (100 IU/mL of penicillin and 100 ug/mL of streptomycin; Sigma), and incubated at 37° C. in a humidified atmosphere containing 5% $CO_2$. Microglia were detached from the astrocyte monolayer by gentle shaking 11-13 days after the dissection, and cultures were 95-98% Mac1 positive.

Phagocytosis Assay

FACS analysis was used to quantify microglial phagocytosis of Aβ1-42. Murine microglia cells were kept in DMEM containing 10% FCS. Twenty-four hours prior to experiments, the FCS concentration was reduced to 1%. The cells (5×10⁶ cells/ml) were incubated with FITC-labeled Aβ1-42 (final concentration 150 μM) in the presence of NA or the βAR agonist isoproterenol (from 10 nM to 10 μM); after 4 hr non cell-associated Aβ was removed by centrifugation at 500×g at 4° C. for 5 min and two washes with ice-cold PBS. The cells were resuspended in 0.02 M acetate buffer pH 5.8 at a concentration of 1×10⁷ cells/mL. Fluorescent signals due to cell adherent Aβ were eliminated by resuspending an aliquot of cells in an equal volume of 1 mg trypan blue/mL (Merck, Darmstadt, Germany) acetate buffer to quench extracellular fluorescence. The mean fluorescence intensity (MFI) was measured on a FACScan (Becton Dickinson, Mountain View, Calif.) equipped with an argon-ion laser (excitation wavelength at 488 nm, laser power 300 mW) and a band pass filter of 530 nm. The data shown is the increase in MFI obtained in the presence of NA or isoproterenol relative to the MFI obtained in control (non-treated) cells. Comparisons were made using unpaired T-test, and P values <0.05 were considered to be significant.

Figure 5:
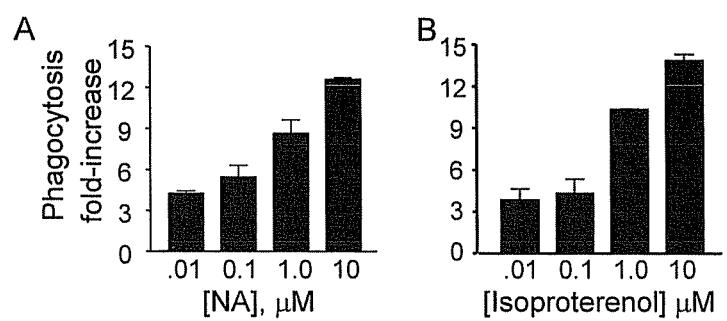
FIGS. 5A and 5B are graphs showing the effects of (FIG. 5A) NA concentration and (FIG. 5B) isoproterenol (β-AR agonist) on phagocytosis of Aβ.

Using primary cultures of neonatal mouse microglia, we observed that accumulation of fluorescently tagged Aβ1-42 was dose dependently increased by NA as well as by the selective βAR agonist isoproterenol (FIG. 5). The data show the fold-increase in intracellular Aβ uptake compared to non-treated cells, and is mean±sd of 4 samples.

The data presented above indicated that degeneration of the LC and associated reduction of brain NA levels with DSP4 influenced the development of amyloid plaques in TgAPP mice. At age 9 months (when plaques first begin to appear in H6 mice) DSP4 treatment increased plaque number 5-fold. The increase in the number of amyloid plaques was associated with an increase in levels of APP C-terminal fragments CTFs, suggesting an increase in APP cleavage, and/or a reduction in peptide clearance. However, the data of DSP4 in vivo, and the data of NA in vitro, suggested effects of NA on processes of amyloid degradation and phagocytosis.

A chronic treatment paradigm was chosen using a relatively low dose (5 mg/kg) which may better reproduce the slow onset of NA dysfunction that is seen with aging in humans, and a gradual rather than abrupt loss of LC neurons. A 70% selective loss of TH positive neurons in the LC was observed, which is comparable to loss seen in AD patients (data not shown).

DSP4 treatment caused a reduction in the mRNA levels of the Aβ degrading enzyme NEP, but not that of IDE. Furthermore, a significant decrease (about 50%) of NEP activity in lysates prepared from DSP4 treated animals was found. The levels of NEP activity measured in cortical lysates were strongly negatively correlated (P<0.0001) to the number of amyloid plaques counted in sagital sections from the same animals, suggesting a causal relationship between these parameters. This is the first demonstration that NA can regulate NEP expression.

Example 7

Effects of DSP4 on TH and IkBα mRNA Levels

In this experiment, the effects of DSP4 on tyrosine hydroxylase (TH) and IkBα expression were analyzed. Adult rat Sprague Dawley rats were treated with the selective neurotoxin DSP4 to lesion locus ceruleus (LC) noradrenergic neurons and deplete cortical NA levels as described in Example 1.

Figure 6:
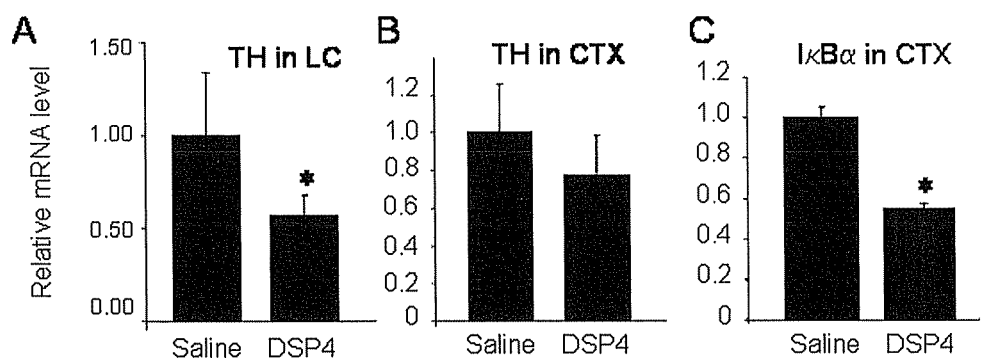
FIGS. 6A through 6C show the effects of DSP4 on mRNA levels of Tyrosine hydroxylase (TH) in the locus ceruleus (FIG. 6A, *, P<0.05), TH in the frontal cortex (FIG. 6B), and IκBα in the frontal cortex (FIG. 6C, *, P<0.01).

RNA samples from control or DSP4-treated rats (n=4 each) were converted to cDNA and analyzed by QPCR for relative levels of tyrosine hydroxylase (TH) (FIG. 6A) in the locus ceruleus (LC). FIG. 6B shows that TH was present in the frontal cortex around the Aβ injection site. FIG. 6C shows the expression of IkB alpha mRNAs in the frontal cortex.

Real Time PCR

Total cytoplasmic RNA from tissues was prepared from cells using TRIZOL reagent according to manufacturer procedures (Invitrogen/GIBCO); aliquots were converted to cDNA using random hexamer primers, and mRNA levels were estimated by quantitative touchdown PCR (QPCR). Conditions were 35 cycles of denaturation at 94° C. for 10 s; annealing at 58-64° C. for 15 s; and extension at 72° C. for 20 s on a Corbett Rotorgene Real-Time PCR unit (Corbett, Australia). The PCR mastermix contained SYBR Green (1 μl diluted 1:10,000 SybrGreen I 10,000× concentrate, Molecular Probes, Eugene, Oreg.). Relative mRNA concentrations were calculated from the takeoff point of reactions using manufacturer's software. Melting curve analysis and agarose gel electrophoresis were performed to ensure production of single and corrected size products. Relative mRNA values were normalized to housekeeping genes, either α-Tubulin (α-Tub), β-Actin (βAct) or glyceraldehyde-3-phosphate dehydrogenase (GDH). The primers used for QPCR (all listed 5' to 3') were:

| | | |
|---|---|---|
| IkBα | GCCTGGCCAGTGTAGCAGTCTT | (SEQ ID NO: 13) |
| | CAGCACCCAAACTCACCAAGTG | (SEQ ID NO: 14) |
| TH | GGGCTTCTCTGACCAGGTGTA | (SEQ ID NO: 15) |
| | GGCAGGCATGGGTAGCATAG | (SEQ ID NO: 16) |
| α-Tub | CCCTCGCCATGGTAAATACAT | (SEQ ID NO: 3) |
| | ACTGGATGGTACGCTTGGTCT | (SEQ ID NO: 4) |
| GDH | GCCAAGTATGATGACATCAAGAAG | (SEQ ID NO: 7) |
| | TCCAGGGGTTTCTTACTCCTTGGA | (SEQ ID NO: 8) |
| β-Act | CCTGAAGTACCCCATTGAACA | (SEQ ID NO: 5) |
| | CACACGCAGCTCATTGTAGAA | (SEQ ID NO: 6) |

Analysis of brain samples showed a significant decrease (57% versus control levels, FIG. 6A) in tyrosine hydroxylase (TH) mRNA levels in the LC as expected since this is the primary site of DSP4-induced neuronal loss. The decrease in TH mRNA has previously been shown to be associated with a reduction in cortical NA levels. There was a slight, albeit not statistically-significant decrease (25% reduction) in cortical TH mRNA levels (P>0.05; FIG. 6B), but a significant decrease (45% versus control values, P<0.01, FIG. 6C) in cortical anti-inflammatory IkBα mRNA levels, which mediates the subsequent exacerbated responses to inflammatory stimuli (FIG. 6C. Thus, DSP4 significantly reduced LC TH (by 43%) and cortical IkBα mRNA levels (by 55%) versus control values (n=4, P<0.01).

Example 8

NOS2 Induction in Wild Type Mice and Effects of Aβ on SMI-32 Staining

NOS2 deficient mice (Nos2tm1Lau) were obtained from Jackson Laboratories. The absence of a functional NOS2 gene (lacking the calmodulin binding domain) was confirmed by PCR analysis. Total cytoplasmic RNA was prepared from brain tissue using TRIZOL reagent (Invitrogen). The primers used for NOS2 detection were NOS2F: CTG TCA CGG AGA TCA ATG TGG (SEQ ID NO:17) corresponding to bases 1415-1435 of mouse NOS2; and NOS2R: AAG GCG TAG CTG AAC AAG GTG (SEQ ID NO:18) corresponding to bases 1848-1868 of mouse NOS2 mRNA. The PCR reaction was expected to yield a 454-bp product when used with the samples from wild type mice, but no PCR product with samples from NOS2 null mice, in which the exon containing the calmodulin-binding domain of NOS2 is replaced by the neomycin resistance gene. PCR conditions were 35 cycles at 95° C. for 10 s, annealing at 58° C. for 15 s and extension at 72° C. for 30 s followed by 5 min at 72° C. in an Eppendorf Thermoreactor (Hamburg, Germany). PCR products were separated by electrophoresis through 1.5% agarose gel electrophoresis containing 0.1 µg/ml ethidium bromide.

Genotyping was performed to confirm identity of NOS2 null and wild type littermates (FIG. 7A), and wild type mice treated with DSP4, and wild type mice treated with DSP4 and injected with oligomeric Aβ1-42 (FIG. 7B). One day later brain sections were analyzed for NOS2 (green) and NeuN (red) staining White arrows indicate neurons labeled with both antibodies.

Wild type and NOS2 null mice were treated with two i.p. injections of DSP4 as described below, and injected with oligomeric Aβ1-42 4 weeks after the second DSP4 injection. One day later brain sections were prepared from the mice, sections from wild type (FIG. 8A) and NOS2 null mice (FIG. 8B) were stained for SMI-32. FIG. 8C shows the quantification of SMI-32 immunoreactivity in n=3 animals per group. *, P<0.01 versus wild-type mice.

Preparation of Aβ

Oligomeric Aβ1-42 was prepared according to the method described. Briefly, Aβ1-42 peptide was resuspended in 1,1,1,3,3,3-hexafluoro-propanol (HFIP, Sigma), then HFIP was allowed to evaporate. Immediately prior to use, the HFIP-treated aliquots were resuspended in anhydrous dimethyl sulfoxide (DMSO, Sigma) followed by bath sonication for 10 min. Aβ1-42 oligomers were prepared by diluting Aβ to 100 µM in phenol red-free Ham's F-12 (Biosource), vortexing for 30 s, and incubating at 37° C. for 24 h.

Surgical Procedures

After acclimation (7-10 days), rats received two intraperitoneal injections (one week apart) of either N-(2-chloroethyl)-N-ethyl-2 bromobenzylamine (DSP4, 5 mg/kg) dissolved in PBS or PBS alone (FIG. 6A). Four weeks after the second treatment, the animals were anesthetized with pentobarbital (50 mg/kg i.p.), and placed in a stereotaxic frame (Stoelting, USA) on a heating blanket. Body temperature was maintained at 37±0.5° C. for the time of surgery. After exposure of the skull, holes were drilled bilaterally at the injection sites and 2 µL of a mixture containing $A\beta_{1-42}$ oligomers (0.5 µg/µL) were injected over a period of 120 s into each cortical hemisphere using a 2 µL Hamilton syringe. Injections were at AP+2.0, L+/−2.5, and V 3.0 mm relative to Bregma. Controls received 2 µL of PBS.

One day after surgery, the animals were killed by an overdose of pentobarbital and brains removed. Half the brain had the injection site excised in a 2 mm coronal slice and further trimmed to approximately 2×2×4 mm encompassing the site of injection. This piece was sonicated in TRIZOL reagent (Invitrogen Inc., Carlsbad, Calif.) for RNA isolation and PCR analysis. The comparable region from the left hemisphere was prepared for immunohistochemical staining Tissue Preparation and Sectioning Brain regions were removed 24 h after Aβ or vehicle injection, and placed in 10% formaldehyde, 10% acetic acid, 80% methanol fixative overnight. Dehydration of 2 mm coronal sections encompassing the site of injection was in a series of 80% and 95% ethanol one hour each followed by 100% ethanol overnight. Two 100% xylene washes were done for 1 hour each and then 1 hour in 60° C. Paraplast Plus (Tyco/Healthcare, Mansfield, Mass.). After a change of Paraplast Plus, tissue was placed in a 60° vacuum oven for 2 hours prior to placing in molds to cool and solidify.

Coronal sections (8 µm thick) located 0, 200 and 400 µm rostral and caudal to the injection site were prepared from paraffin embedded tissue, floated onto slides, dried 2 h, heated to 54° C. for 2 h on a slide warmer and stored at 22° C. Slides were deparaffinized with xylene and ethanol. Antigen unmasking was done with 10 mM Na Citrate buffer, pH 6.0, heated in a microwave, kept at 100° C. for 10 min. and then cooled to room temperature for 20 min. Sections were immediately processed for immunohistochemistry.

Immunohistochemistry

Slides were washed for 5 min. with PBS and blocked with 5% normal donkey serum in PBS at room temperature for 30 min. Primary antibodies were diluted in 1% normal donkey serum in PBS. Sections were incubated with primary antibodies (mouse mAb anti-SMI-32, a marker for neural damage, 1:1000 dilution; or mouse mAb anti-NOS2, 1:200 dilution) at 37° C. for 1 hour. Sections were washed 3 times with PBS. Secondary antibodies (donkey anti-mouse Rhodamine Red-X (RRX) conjugated and donkey anti-goat FITC conjugated; Jackson ImmunoResearch Inc., West Grove, Pa.) were pre-absorbed to minimize cross reactivity. Sections were incubated with secondary antibodies (diluted 1:200 in PBS with 1% normal donkey serum) for 1 hour at 37° C. Slides were washed 3×5 minutes with PBS and post-fixed in 3.7% formaldehyde in PBS for 20 min. Autofluorescence was quenched with 50 mM $NH_4Cl$ in PBS for 15 min. Nuclei were stained using DAPI (400 ng/mL in PBS for 3 min). Vectashield mounting fluid (Vector Laboratories Inc., Burlingame, Calif.) was used. Images were obtained on a Zeiss Axioplan2 fluorescence microscope equipped with an Axiocam MRm digital camera and Axiovision 4.2 imaging software.

Data Analysis

Quantitative analysis of NOS2 positively staining cells was performed as described above. In brief, NOS2 positive containing neurons having large cell bodies were counted in 5 sections having a defined distance (0, 200 and 400 µm rostral and caudal) relative to the level of cortical injection, in brain sections from at least 3 or 4 animals per group. The number of cells within the respective fields was determined using a counting grid, and cells within the needle tract were not counted. Quantification of SMI-32 immunoreactivity was performed using Zeiss Axio-Vision software (Carl Zeiss International). The area corresponding to cells with positive staining (over a background threshold value which was determined from images where primary antibody was omitted) under 10× magnification images was measured and the ratio of area stained to total area was calculated. The results are the average of 4 measurements of images corresponding to the same area of slides.

Figure 7:
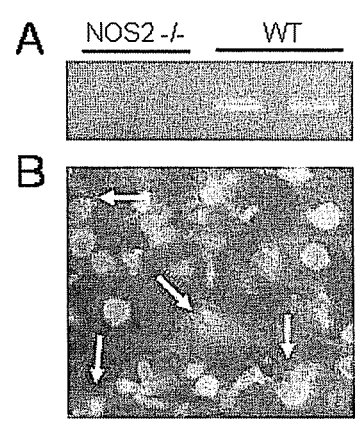
FIG. 7A is a photoimage of ethidium bromide stained gel demonstrating genotyping confirmation of NOS2 null and wild type littermates.
FIG. 7B is a photomicrograph showing NOS2 and NeuN staining in sections from wild type mice treated with DSP4. White arrows indicate neurons labeled with both antibodies.
Figure 8:
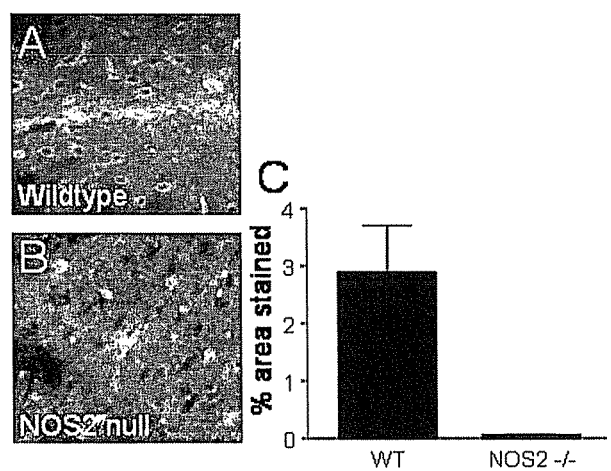
FIGS. 8A and 8B are photomicrographs showing the effects of Aβ on SMI-32, a marker for neuronal damage, staining in wild type (FIG. 8A) and NOS2 null mice (FIG. 8B).
FIG. 8C is a graph showing the quantification of SMI-32 immunoreactivity in the two groups.
Figure 9:
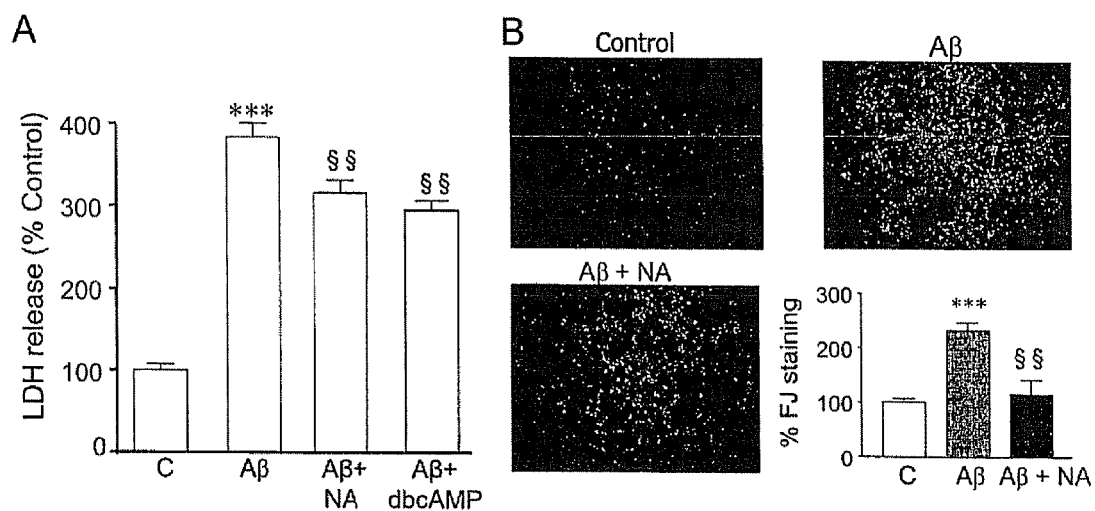
FIGS. 9A and 9B show that NA reduces Aβ induced damage in primary neurons.

The effects of Aβ1-42 injection into NOS2 deficient mice are shown in FIG. 7. In DSP4-treated, wild type mice, Aβ1-42 injection increased neuronal NOS2 staining, similar to what was observed in DSP4 treated rats, and likewise increased SMI-32 staining (FIG. 8). In contrast, injection of Aβ1-42 into DSP4-treated, NOS2 deficient mice did not cause a significant increase in SMI-32 immunoreactivity. Together, these findings suggest that NOS2 expression (and activity) is an important factor in the development of inflammatory response and neuronal damage due to Aβ.

Example 9

NA Depletion Exacerbates EAE

The effects of brain NA depletion on the progression of EAE (a mouse model of Multiple Sclerosis (MS)) were assessed in this experiment. C57B16 female mice were treated with the selective neurotoxin DSP4 (50 mg/kg; i.p., twice one week apart) then immunized with MOG peptides 2 weeks later to develop EAE (FIG. 10A, 10B). More specifically, a chronic form of EAE disease was actively induced in the female C57B16 mice using synthetic myelin oligodendrocyte glycoprotein peptide 35-55 (MOG$_{35-55}$; MEVGWYRSPFSRVVHLYRNGK (SEQ ID NO:19) purchased from Anaspec, San Jose, Calif.). Mice were injected subcutaneously with an emulsion of 300 μg MOG$_{35-55}$ dissolved in 100 μL PBS, mixed with 100 μL complete Freund's adjuvant containing 500 μg of *Mycobacterium tuberculosis* (Difco, Detroit, Mich.). The animals then received an injection of 200 ng pertussis toxin (PT, List Biochemicals, Campbell, Calif.) in 200 μL PBS. Two days later the mice received a second PT injection, and one week later a booster MOG$_{35-55}$ injection was given. The data are combined from 2 separate studies, and show mean±se of clinical scores and daily incidence for control and treated mice.

Figure 10:
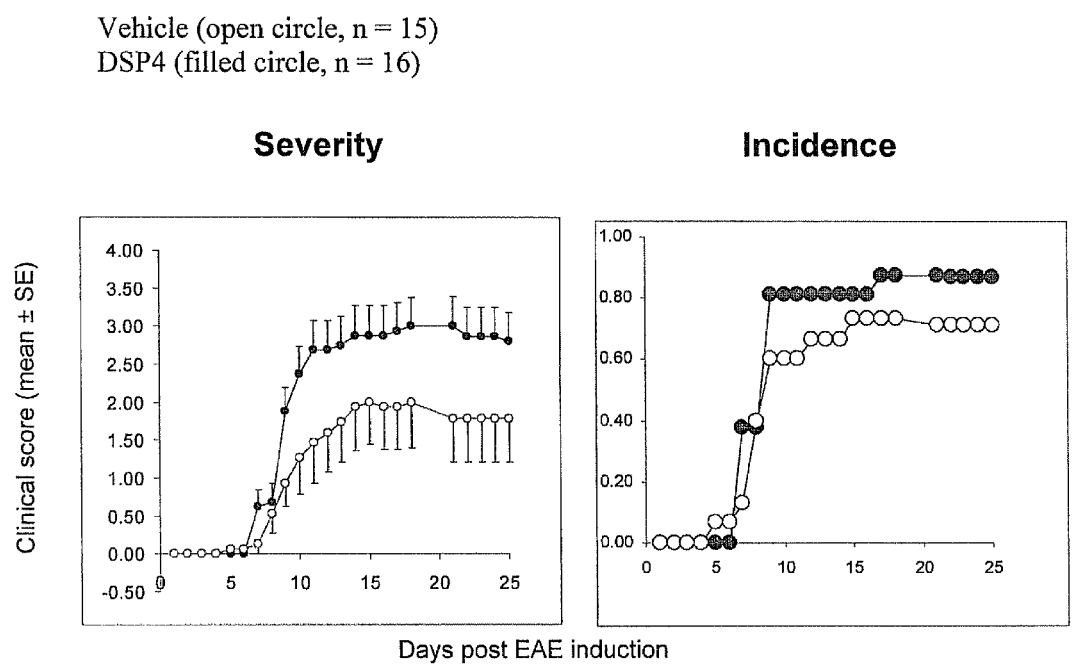
FIG. 10 shows the effects of NA depletion using DSP4 in experimental autoimmune encephalomyelitis (EAE), a mouse model of Multiple Sclerosis (MS). The left panel shows the effects on average clinical disease and the right panel shows the effect on the average disease incidence, x-axis indicating days post EAE induction, i.e., days post treatment of mice with the EAE-inducing peptide MOG.

The results showed that the clinical signs in DSP4-treated mice appeared sooner and were more severe than in vehicle treated mice (FIG. 10). DSP4 caused long-lasting and selective reduction of brain NA content (with fewer effects on peripheral NA levels that recovered within 1 week), which suggested that modulating NA levels in the CNS can influence EAE. The fact that the incidence of disease was similar in the 2 groups suggests that DSP4 treatment did not influence T-cell priming or activation, but instead modified inflammatory responses in brain.

Example 10

Effects of Increased NA on EAE

Figure 11:
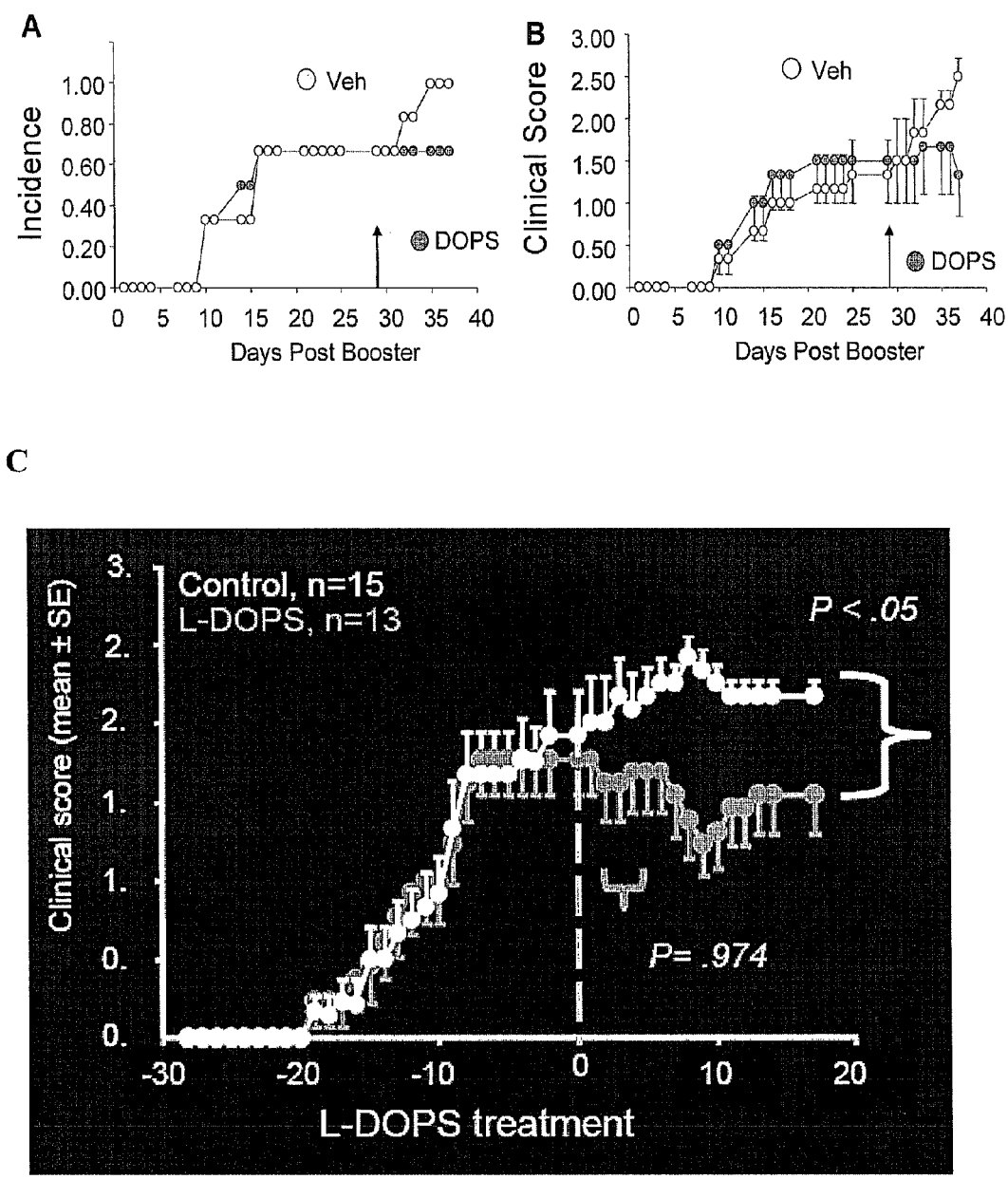
FIGS. 11A-C show the effects of L-DOPS on clinical symptoms of EAE. Arrows in FIGS. 11A and B and a dashed line in FIG. 11C indicate the first day L-DOPS was i.p. injected into the animals. P=0.974 one way rm np ANOVA (day 0 to end).

To test whether increased NA derived from the NA precursor L-DOPS could provide benefits in EAE, C57B16 mice were immunized with MOG$_{35-55}$ peptide using standard procedures. At day 29 (FIG. 11A, arrow) after the booster MOG, 6 mice received daily injections of L-DOPS (using an intermediate dose of 200 mg/kg s.c.; plus 125 mg/kg bensazeride i.p. to block peripheral conversion to NA); control mice received saline. In the saline group, 4/6 mice were ill on day 29, and by day 36 all 6 were ill (FIG. 11A); the average clinical score increased from 1.3±0.4 (mean±se) on day 29 to 2.3±0.2 on day 37 (FIG. 11B). In the L-DOPS group, 4/6 mice were ill on day 29 and incidence did not further increase. During treatment, scores of 2 of the 4 mice improved, and the average score decreased from 1.5±0.5 on day 29 to 1.2±0.4 on day 38. Similar results were obtained in a separate experiment as shown in FIG. 11C. These results showed that increasing NA could have beneficial therapeutic effects even at later stages of EAE.

Example 11

Effects of NA and cAMP on Oligodendrocyte Maturation and Neurogenesis

It has been known that agents that increase cyclic adenosine monophosphate (cAMP) have maturation and survival effects on primary oligodendrocytes (OLGs) and OLG cell lines. However, the effects of NA on the extracellular factors which induce OLG maturation, such as bone morphogenetic proteins (BMP) family, are not well known.

Figure 12:
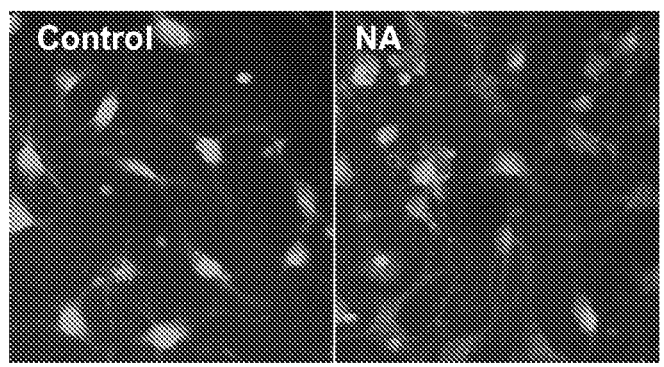
FIGS. 12A through 12D show the effect of NA on bone morphogenic protein (BMP) expression in neural cells.
Figure 12:
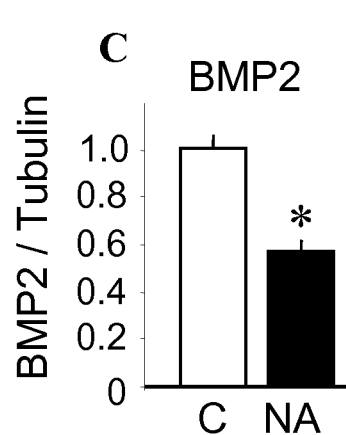
Figure 12:
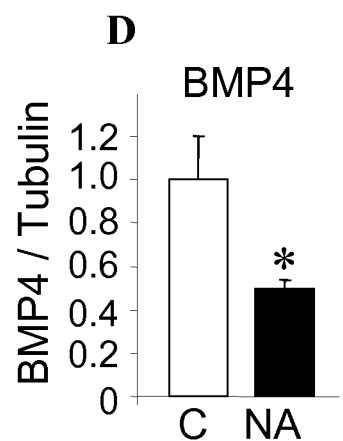

Initial studies were carried out to identify treatments that influence OLG maturation using primary oligodendrocyte progenitor cells (OPCs) from E13 mouse pups. The cells were isolated as E13 neurospheres, and were shifted to OLG commitment (Oligospheres) by culture in PDGFα and bFGF. E13 Oligospheres were cultured on polylysine coated slides in media (containing bFGF and PDGFα) in the presence or absence of 25 μM NA. After 2 days the cells were fixed and stained with antibody to MBP (FIGS. 12A and 12B). After 2 days in the presence of NA, increased network of OPC processes, and a general increase in fine membrane sheets were observed, suggesting that NA accelerated OPC maturation.

Figure 13:
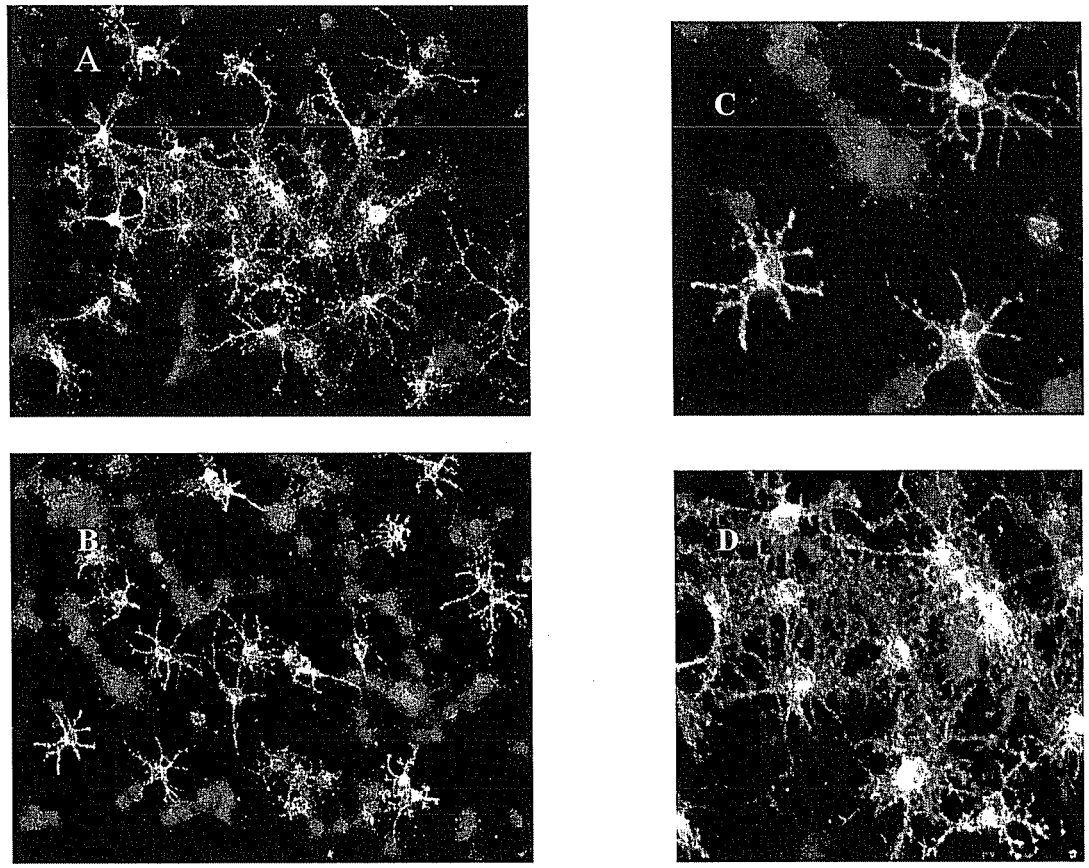
FIGS. 13A through 13D show the effect of NA on P1 OPC maturation.
Figure 14:
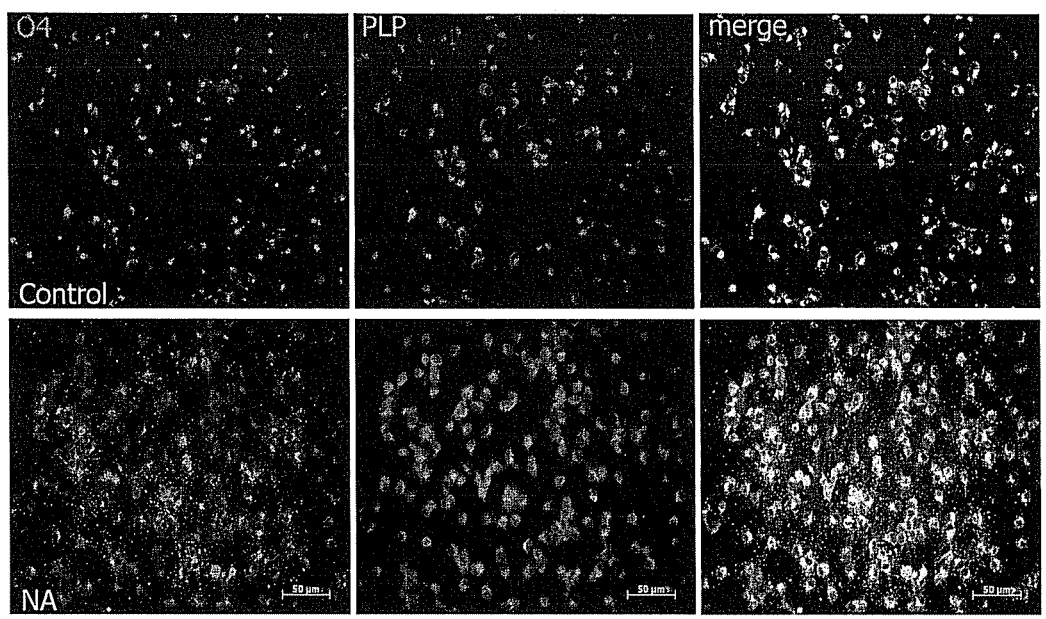
FIG. 14 is photomicrographs of oligospheres immunostained with antibodies to Oligodendrocyte Marker 04 and PLP to show that NA increases oligosphere maturation into myelinating oligodenderocytes. The top panels are untreated OPCs. The bottom panels show increased OPC maturation after 24 hour treatment with 30 μM NA.

Further studies were carried out in which the oligospheres were cultured on polylysine coated slides in media (containing bFGF and PDGFα) in the presence or absence of 20 μM NA. After 24 hours the cells were fixed and stained with antibodies for PDGFRa, Oligodendrocyte Marker O4 and PLP (FIGS. 13 and 14). After 24 hours in the presence of NA, increased network of OPC processes, and a general increase in fine membrane sheets were observed, further suggesting that NA accelerated OPC maturation.

Figure 15:
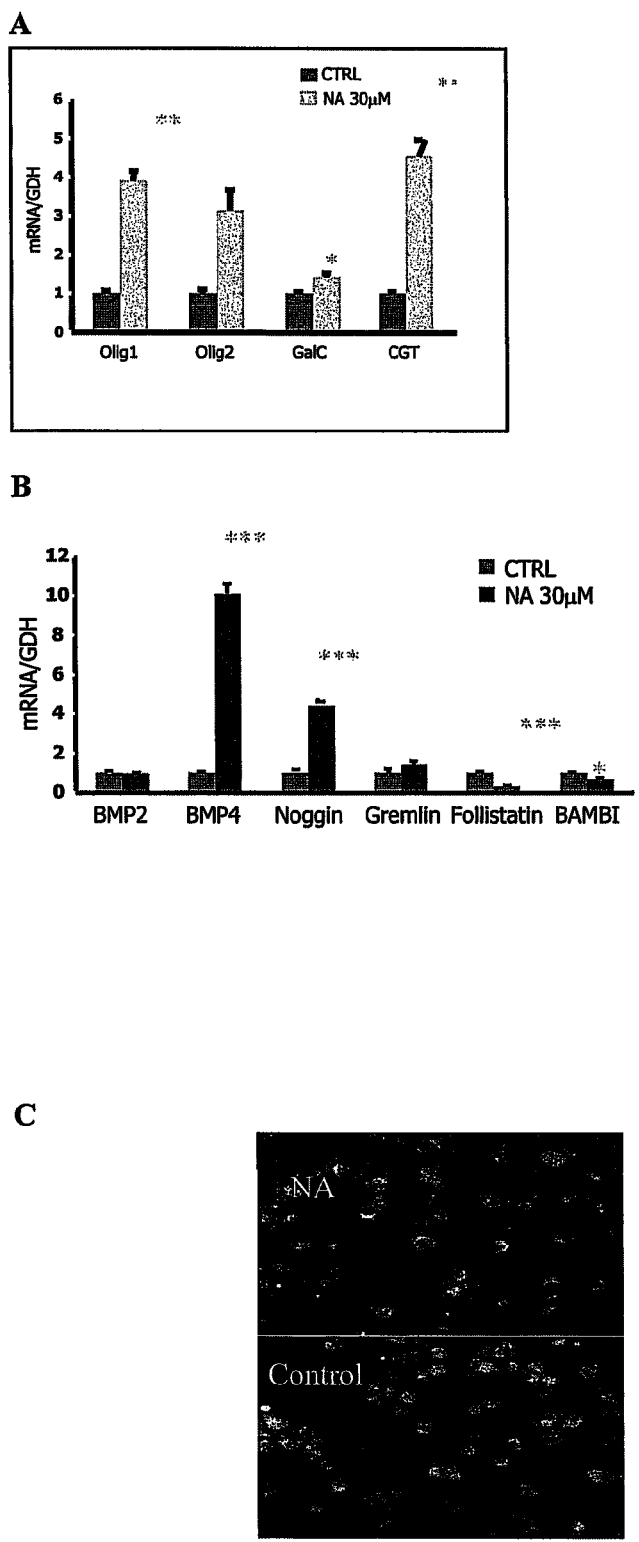
FIGS. 15A through 15C are graphs showing changes of mRNA expression of indicated genes in P1 OPCs after treatment with NA by quantitative polymerase chain reaction (QPCR) analysis.

Additional studies were carried out in which QPCR analysis was performed for BMPs, BMP antagonists and myelin genes on P1 OPCs treated with saline or NA. The QPCR condition and primers are as described in Example 3. For QPCR experiments, RNA levels were calculated from QPCR take-off points, normalized for RNA values obtained for GDH; the average value for the vehicle treated RNA levels was set to 1.0. Comparisons were made using unpaired T-test, and P values <0.05 were considered to be significant. (FIGS. 15A and 15B). The increased levels of Olig1, Olig2, GALc and CGT demonstrate that NA treatment increases OPC maturation.

The presence of astrocytes in the cultures suggested that NA could influence release of maturation factors. Primary astrocytes were treated with 100 μM NA for 24 hr then mRNA levels of bone morphogenic proteins BMP2 and BMP4 (which normally inhibit oligodendrocyte maturation) were measured by QPCR. As shown in FIGS. 12C and 12D, BMP2 and BMP4 mRNA levels were decreased in astrocytes treated with NA. Data is mean±sd of n=2-3 experiments, and normalized to values for β-tubulin measured in the same samples.

Figure 16:
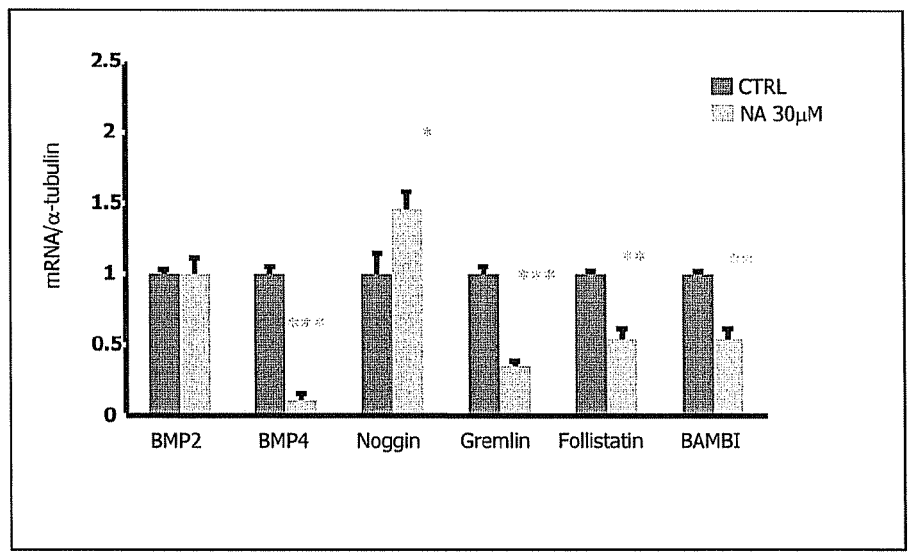
FIG. 16A is a graph showing the modulation of BMPs and BMP antagonists mRNA expression in primary astrocytes due to treatment with NA by QPCR analysis. *, P<0.05, , P<0.01, *, P<0.001, t test, n=3.
FIG. 16B are photomicrographs of primary astrocytes treated with NA and non-treated primary astrocytes immunostained with antibody specific for Noggin to show that NA increases Noggin protein expression in astrocytes.
Figure 16:
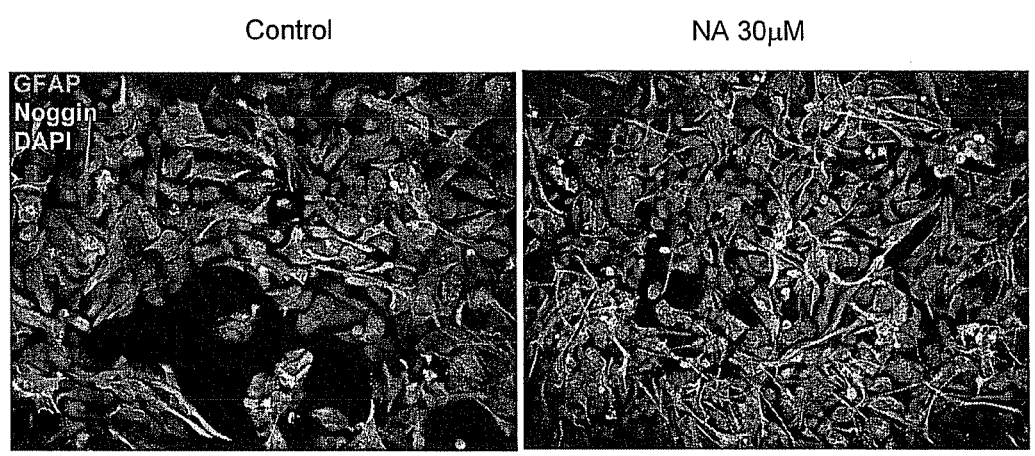

Further studies were carried out in which primary astrocytes were treated with 30 μM NA for 24 hours then mRNA levels of bone morphogenic proteins BMP2 and BMP4, Noggin, Gremlin, Follistatin and BAMBI were measured by QPCR (FIG. 16A). The results confirmed that BMP4 mRNA levels were decreased, whereas the Noggin mRNA levels were increased, in NA treated primary astrocytes (FIG. 16A). Staining with Noggin antibody was also performed on the cultured primary astrocytes which confirmed increased Noggin expression in NA-treated primary astroctyes (FIG. 16B).

Thus, potential beneficial effects of NA in EAE (and MS) are not limited to reduction of inflammatory responses or neuronal damage, but may also include positive effects on neural precursor cells (NPCs) such as OPCs and maturation into myelinating oligodendrocytes.

Example 12

Pathophysiological Changes in EAE and MS Disease

Animal Models of EAE Disease

A chronic form of EAE disease was actively induced in 8-week old female C57B16 mice as described in Example 9. To assess disease severity, clinical signs were scored as follows: 0 indicated no clinical signs, 1 indicated a limp tail, 2 indicated an impaired righting of the animal, 3 indicated paresis of one hind limb, 4 indicated paresis of two hind limbs, and 5 indicated the death of the animal.

Human MS Tissue Specimens

Tissue specimens containing the area of the LC were obtained from autopsied brains of 5 multiple sclerosis patients and 6 normal controls. A coronal section was dissected from the brainstem beginning at approximately +23 mm rostral of the obex (the point at which the IVth ventricle narrows to become the central canal of the spinal cord) and extending rostrally approximately 5 mm. This area contains the majority of the LC neurons (Paxinos and Mai 2004). Age, sex, disease, and autolysis time are listed in Table 1. Samples were kept stored at −80° C. until use.

TABLE 1

| Patient ID | Age (yr) | Sex | Disease | Autolysis Time (hr) |
|---|---|---|---|---|
| MS1 | 49 | F | SP | 15.0 |
| MS2 | 54 | M | SP | 15.0 |
| MS3 | 70 | M | SP | 23.0 |
| MS4 | 70 | F | CP | 9.0 |
| MS5 | 82 | F | CP | 20.8 |
| C1 | 93 | F | | 20.3 |
| C2 | 77 | M | | 12.3 |
| C3 | 54 | M | | 19.0 |
| C4 | 81 | F | | 11.3 |
| C5 | 73 | F | | 12.0 |
| C6 | 70 | M | | 12.0 |

SP, secondary progressive MS;
CP, chronic progressive MS

Measurements of Noradrenaline Levels in EAE and MS Samples

Cell lysates were prepared from samples of frontal cortex (FC), spinal cord (SC), and LC of EAE and non-EAE mice. From human samples, a combined cell lysate was prepared from 3 min tissue punches taken from the area located immediately ventral and lateral to the LC (primarily consisting of the central tegmental tract, the medial longitudinal fasiculus, and the central gray of the pons). The LC itself was not included since that was used for immunohistochemical studies. Tissues were homogenized on ice in 40 volumes of 0.01N HCl, 1 mM EDTA and 4 mM sodium metabisulfite. ELISA for NA was performed per manufacturer's instructions (Rocky Mountain Diagnostics Inc., Colorado Springs, Colo.).

Figure 17:
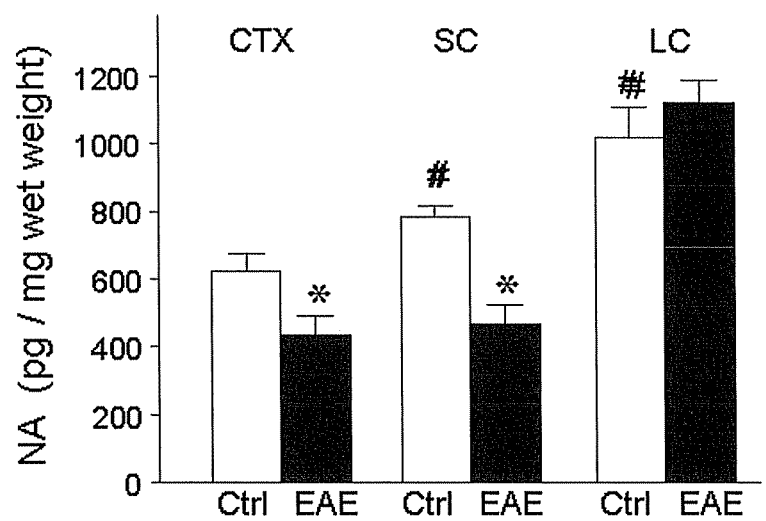
FIG. 17 is a graph showing decreased cortical and spinal cord NA levels in EAE mice. NA levels were quantified by specific ELISA in samples from frontal cortex (CTX: n=10 controls, n=9 EAE); spinal cord (SC: n=15 controls, n=12 EAE); and locus coeruleus (LC: n=6 controls, n=4 EAE). Data is expressed as pg NA per mg wet weight tissue and are represented as means±SEM; *, P<0.05 versus control; #, P<0.05 versus control CTX (unpaired T-test).

NA levels were measured by specific ELISA in homogenates prepared from the LC, the frontal cortex (FC), and spinal cords (SC) of control and MOG-immunized EAE mice 60 days after immunization, at which point the EAE mice had moderate to severe disease severity (clinical scores of 2.0 to 4.0). In control mice, NA levels were lowest in the FC, higher in SC, and greatest in the LC. A significant decrease was observed in both the FC and SC of EAE mice as compared to age and sex matched controls (FIG. 17). Interestingly in the LC there was a trend towards higher levels of NA in EAE mice compared to age-matched controls. These results point to perturbations of NA level in the CNS during EAE, with increases in LC possibly due to compensatory activity of noradrenergic neurons as reported in other mouse models (Szot et al., 2009, "Age-dependent changes in noradrenergic locus coeruleus system in wild-type and APP23 transgenic mice," *Neurosci. Lett.* 463: 93-97).

Figure 18:
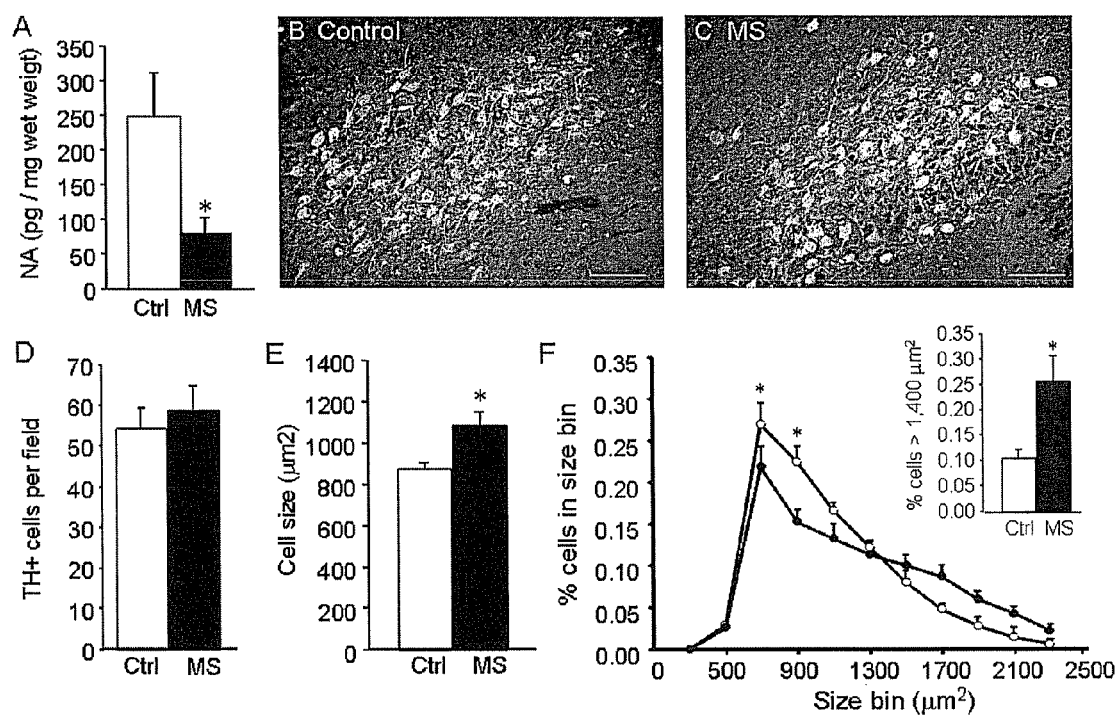
FIGS. 18A through 18F show locus coeruleus (LC) dysfunction in MS patients.

Measurement of NA levels in samples from the adjacent ventral and lateral portions of the pons from five human multiple sclerosis samples and five human controls showed a significant reduction of NA levels in multiple sclerosis samples (FIG. 18A).

Immunohistochemistry

Immunohistochemical staining was carried out to assess glial activation and inflammation in the LC and surrounding area in EAE mice and human MS brain samples. Mouse and human brain samples were fixed overnight in 4% PFA in 0.1M phosphate buffer pH 7.6, dehydrated through alcohols and xylenes, then embedded in paraffin. Serial sagittal sections (8 μm) were taken through the complete area of mouse LC. Serial 8 μm coronal sections were collected from human tissue, and organized such that a total of 9 sections per brain were stained for each antibody, each section separated from the next by 280 μm and the total series spanning approximately 2.24 mm.

Following paraffin removal, antigen retrieval was accomplished by boiling in 10 mM citrate buffer for 10 min, followed by a single wash in PBS containing $Ca^{2+}/Mg^{2+}$, and then blocked with 5% normal donkey serum. Sections were incubated at 4° C. overnight with primary antibodies rat mAb anti-human GFAP B2.210 diluted in 1% normal donkey serum at 1:300 (Trojanowski et al., 1986, "An immunocytochemical study of normal and abnormal human cerebrospinal fluid with monoclonal antibodies to glial fibrillary acidic protein," *Acta Cytol.* 30: 235-239); rabbit polyclonal anti-tyrosine hydroxylase at 1:300 (Pel-Freeze, Rogers, Ak.); mouse monoclonal SMI-32 against non-phosphorylated neurofilament at 1:500 (Sternberger Monoclonals Inc, Lutherville, Md.), or goat anti-NFkB p65 subunit at 1:50 (Santa Cruz Biotechnology, CA). After washing, sections were incubated for 45 min at 37° C. with appropriate secondary antibodies pre-absorbed to reduce cross reactivity (Jackson ImmunoResearch), conjugated to either RRX or FITC and used at a concentration of 1:200. Sections were washed, briefly post-fixed in 3.7% PFA, quenched in 50 mM ammonium chloride, then final washes were done in PBS containing 800 ng/ml DAPI. Sections were covered with cover-slips using Vectashield mounting fluid (Vector Laboratories Inc., Burlingame, Calif.).

1. GFAP Staining

Figure 19:
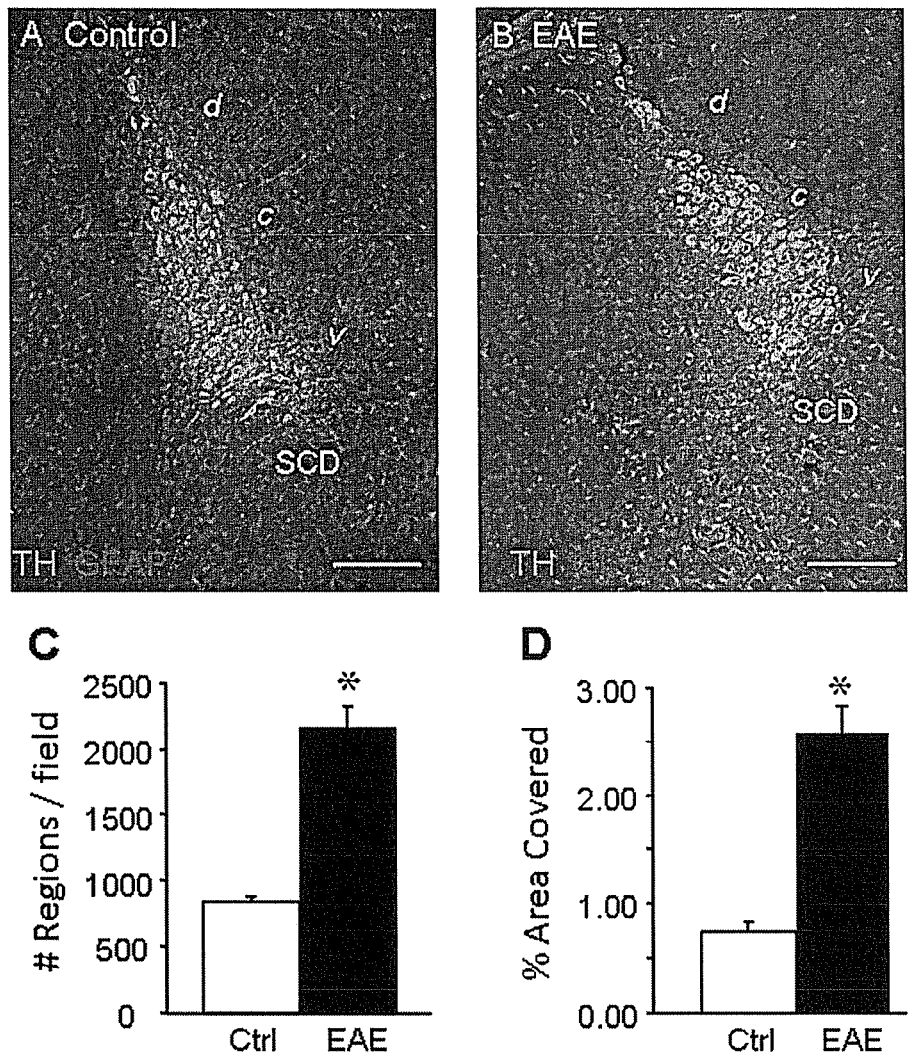
FIGS. 19A through 19D show increased GFAP staining in the LC of EAE mice.

In the dorsal and central parts of the LC, low levels of GFAP staining were observed in control and EAE mice. However, in the ventral LC and the area immediately below which contains noradrenergic subcoeruleus dorsal (SCD) neurons and fibers, both the number of GFAP+ stained cells and processes, and the total area covered by GFAP+ staining were significantly increased in the EAE mice (FIG. 19). The fact that increased GFAP+ staining was primarily observed in the ventral LC and SCD areas, both of which send projections to the spinal cord (Proudfit and Clark, 1991, "The projections of locus coeruleus neurons to the spinal cord," *Prog Brain Res.,* 88: 123-141; Tanaka et al., 1997, "Development regulation of spinal motoneurons by monaminergic nerve fibers," *J. Peripher. Nerv. Syst.* 2: 323-332; Holstege and Bongers, 1991, "Ultrastructural aspects of the coeruleo-spinal projection," *Prog. Brain Res.* 88:143-156), and not in the central and dorsal portion of the LC suggests that increased inflammation is associated with topographically defined TH+ neurons and is not a general consequence of diffuse inflammation in EAE.

Figure 20:
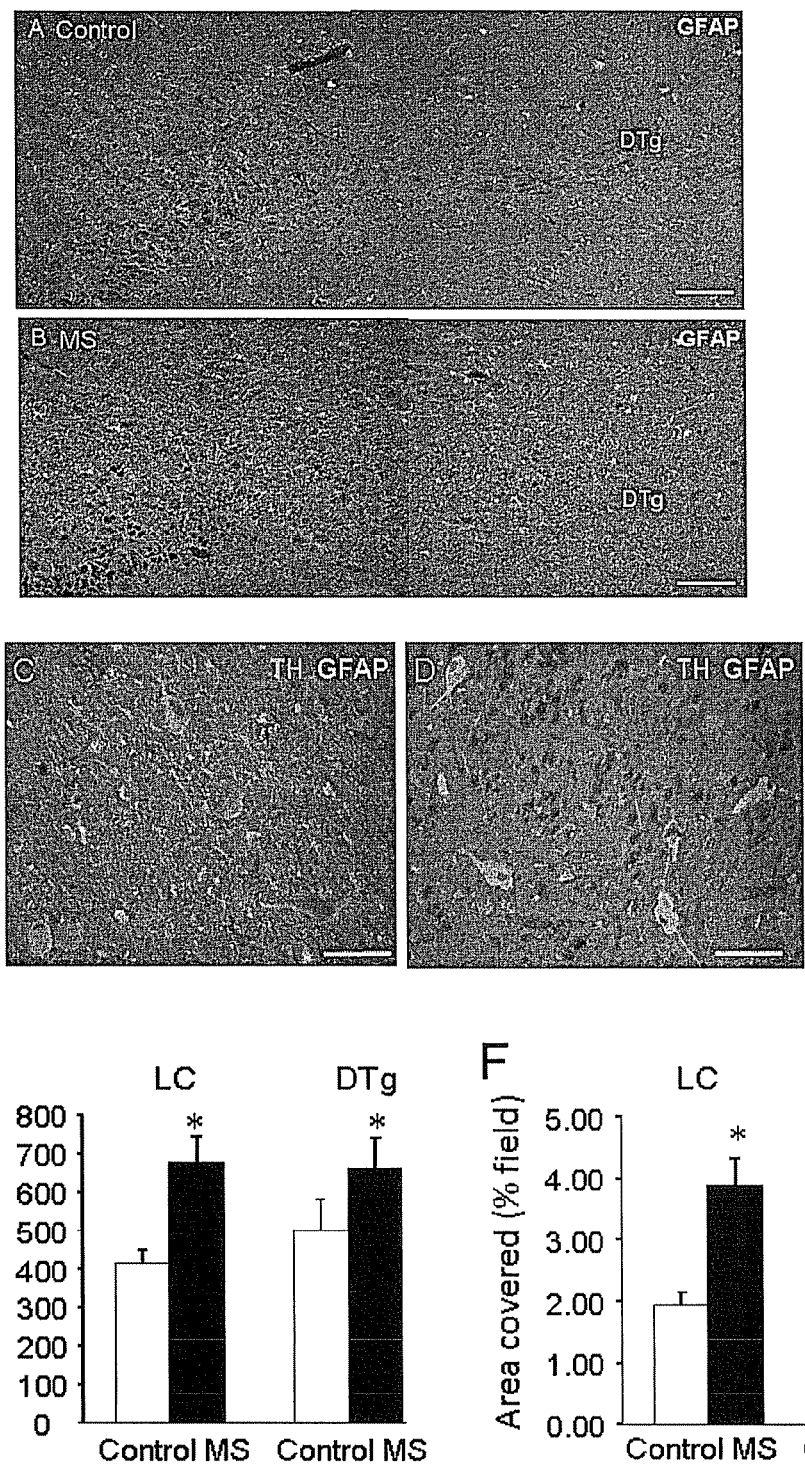
FIGS. 20A through 20F are photomicrographs and graphs showing GFAP and TH staining in the LC of MS and control patients.

To determine if comparable inflammation or neuronal damage occurred in multiple sclerosis patients, immunochemical staining of brain samples from 5 multiple sclerosis patients and 6 controls (FIGS. 20A and 20B) was performed. Increased GFAP+ staining was observed both in the LC itself as well as in the medially located dorsal tegmental nucleus (DTg) in multiple sclerosis patients compared to controls. GFAP+ staining was detected around TH+ stained neurons in the LC but not outside of the LC (FIGS. 20C and 20D). Quantitative analysis showed a significant increase in the number of GFAP positively stained objects detected (FIG. 20E) and in the % area stained section (FIG. 20F).

2. NFkB Staining

Figure 21:
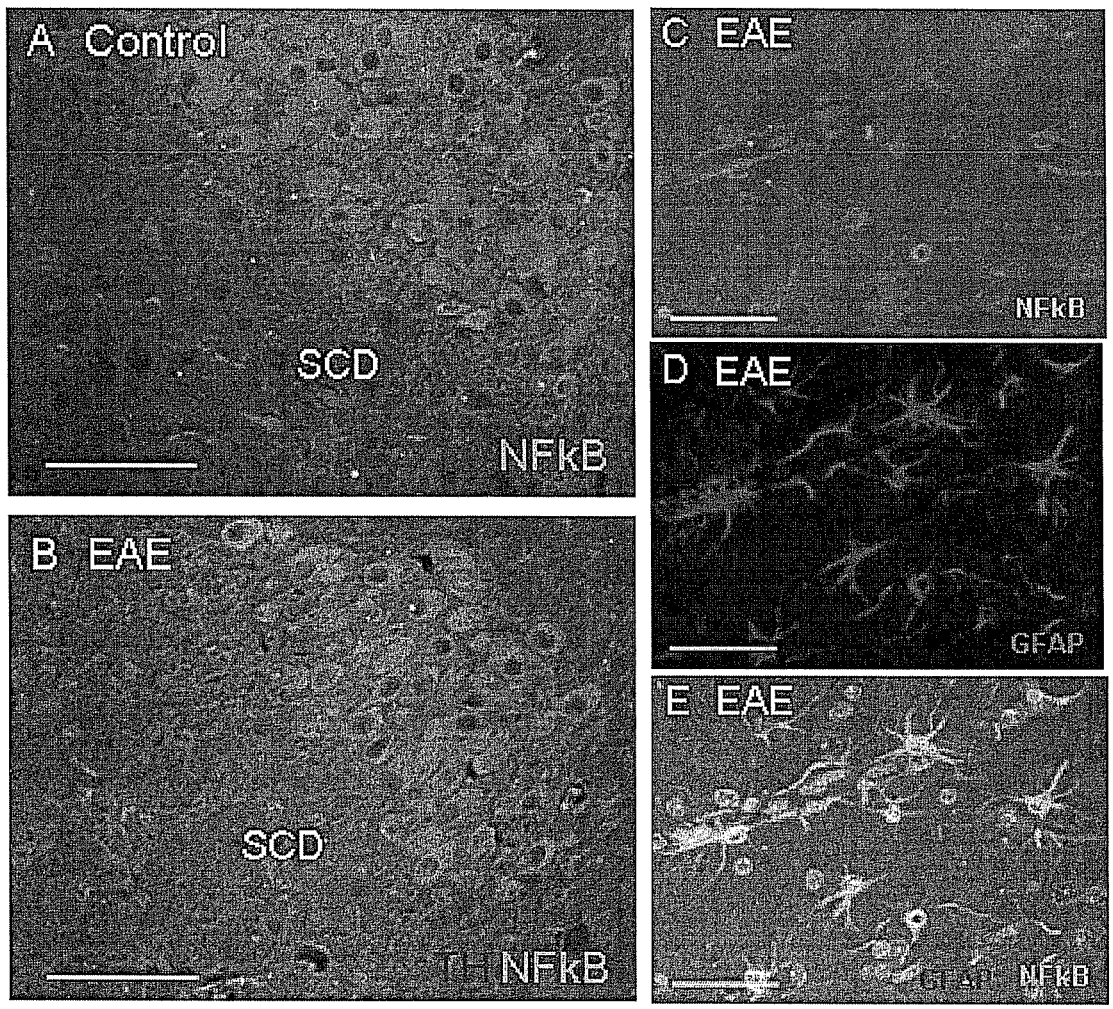
FIGS. 21A through 21E are photomicrographs showing increased NFκB staining in LC of EAE mice.

Staining for the p65 subunit of the inducible transcription factor NFκB also showed increased staining in EAE as compared to control mice (FIGS. 21A-21E). Similar to GFAP, the greatest NFκB staining was in the ventral LC and SCD areas (FIGS. 21A-21B), and was co-localized with GFAP+ stained cells (FIGS. 21C-21E).

3. SMI-32 Staining

Figure 22:
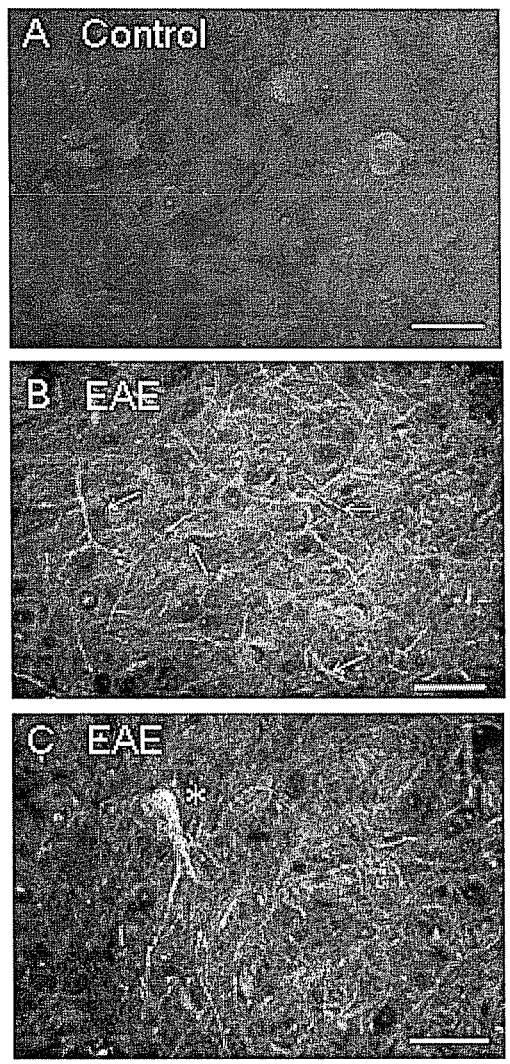
FIGS. 22A through 22C are photomicrographs showing increased staining for non-phosphorylated neurofilament protein, a marker of neuronal damage, in the LC of EAE mice. The photomicrographs are images from the midcentral portion of the LC from control (FIG. 22A) and EAE mice (FIGS. 22B and 22C), which show increased SMI-32 staining throughout this area in axons with beaded appearance (arrows, FIG. 22B) and in cell bodies with spheroid appearance (asterisk, FIG. 22C). Scale bars are 50 µm.

An assessment of neuronal damage in the LC was obtained using antibody SMI-32 which detects non-phosphorylated neurofilament H protein in cell bodies, dendrites, and thick axons and has been used as a marker of injury, stress, or vulnerability in EAE and MS samples (Dziedzic et al., 2010, "Wallerian Degeneration: A Major Component of Early Axonal Pathology in Multiple Sclerosis, Brain Pathol. 20: 976-985; Lindner et al., 2009, "Chronic toxic demyelination in the central nervous system leads to axonal damage despite remyelination," Neurosci. Lett. 453: 120-125; Mahad et al., 2009, "Mitochondrial changes within axons in multiple sclerosis," Brain 132: 1161-1174; Budde et al., 2008, "Axonal injury detected by in vivo diffusion tensor imaging correlates with neurological disability in a mouse model of multiple sclerosis," NMR Biomed. 21: 589-597; Irvine and Blakemore, 2006, "Age increases axon loss associated with primary demyelination in cuprizone-induced demyelination in C57BL/6 mice", J. Neuroimmunol. 175: 69-76; Gilgun-Sherki et al., 2003, "Riluzole suppresses experimental autoimmune encephalomyelitis: implications for the treatement of multiple sclerosis," Brain Res. 989:196-204). SMI-32 staining was observed in EAE, but not control sections in the LC (FIG. 22A), and revealed alterations in neuronal morphology including beading (FIG. 22B) and spheroids (FIG. 22C).

Figure 23:
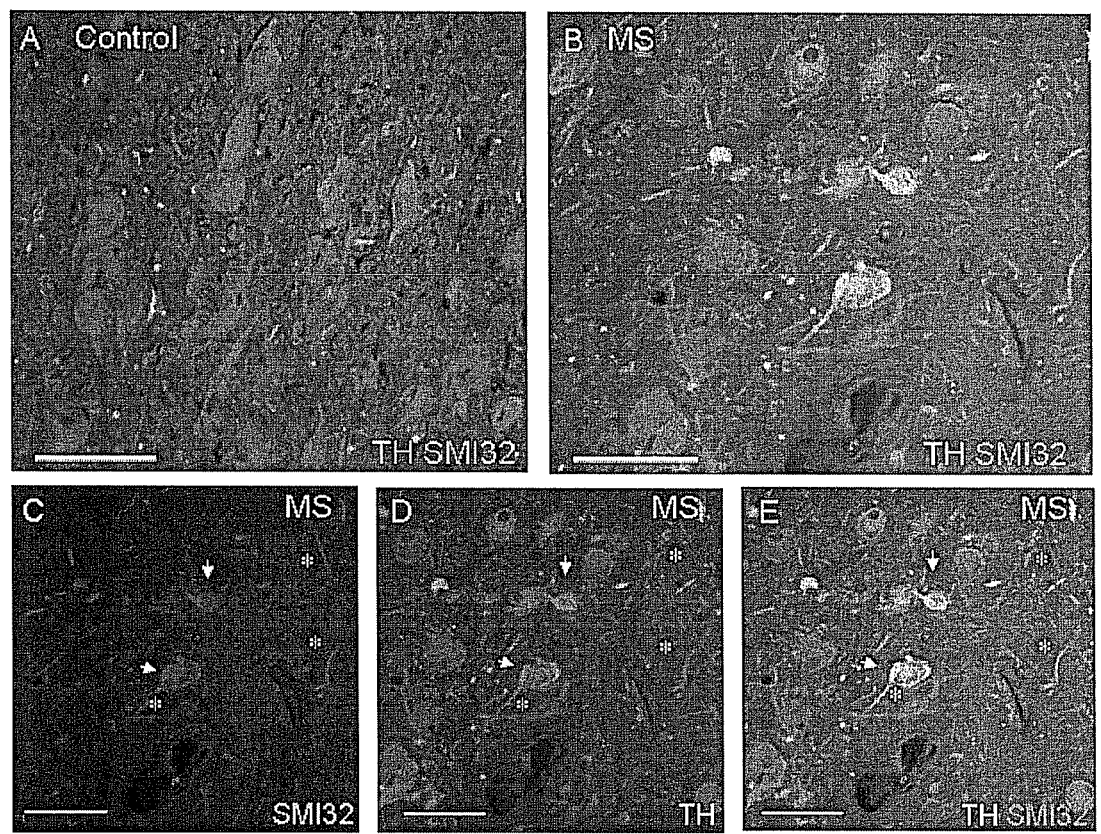
FIGS. 23A through 23E are photomicrographs showing increased staining for non neurofilaments (non-phosphorylated non-neurofilament H, detected by SMI32), a marker of neuronal injury, in LC of human MS brains. Representative images are shown of LC from control (FIG. 23A) and MS patients (FIG. 23B).

To determine if comparable neuronal damage occurred in multiple sclerosis patients, immunochemical staining of brain samples from 5 multiple sclerosis patients and 6 controls was performed. As found for EAE, an increase in SMI-32 staining was observed in the LC region of MS brains compared to controls (FIGS. 23A, 23B), indicative of neuronal damage; and SMI-32 staining could be co-localized with TH+ stained cell bodies (FIG. 23C, arrowheads) and their processes (FIG. 23D, asterisks).

4. TH Staining

Figure 24:
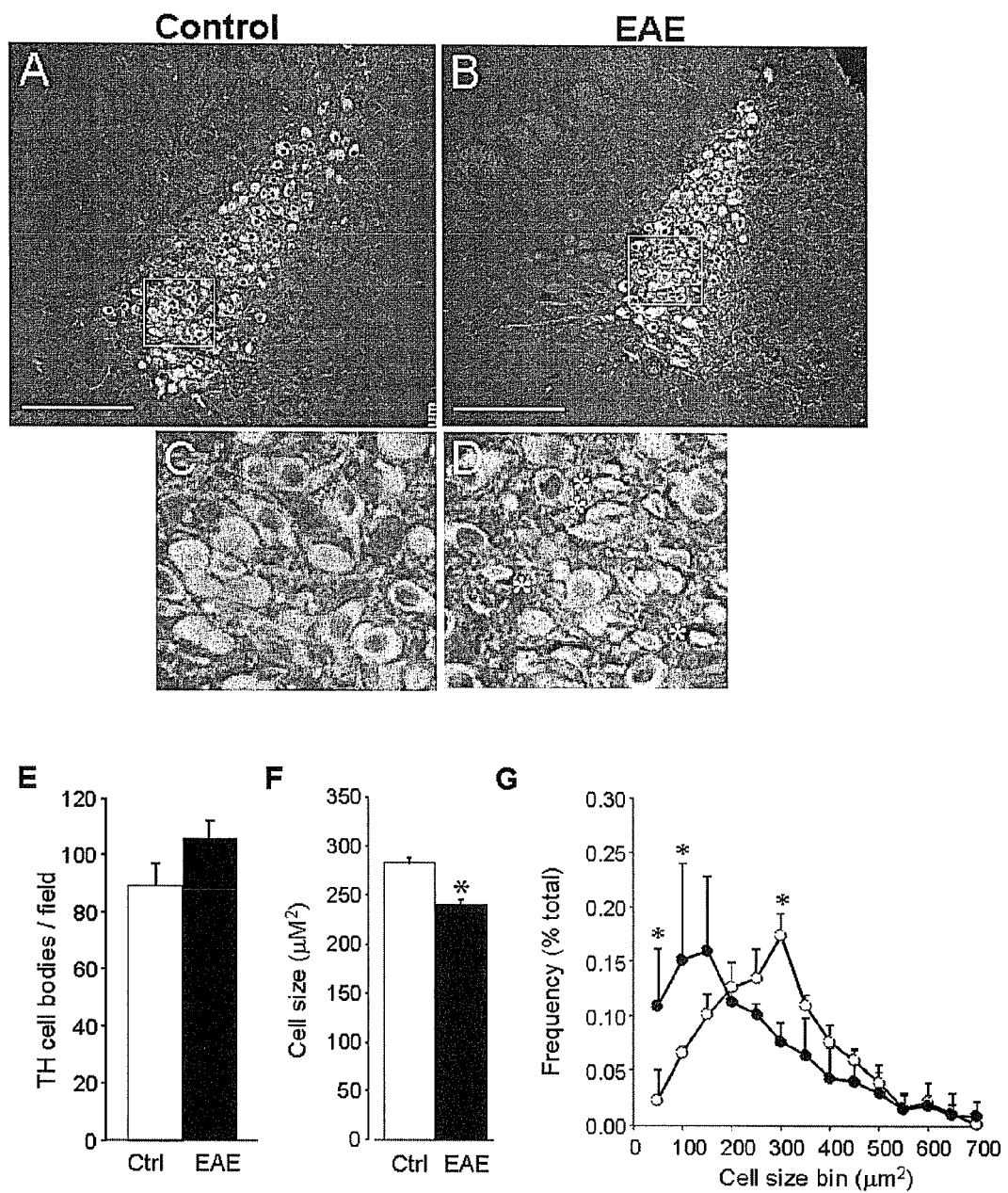
FIGS. 24A through 24G are photomicrographs and graphs showing that TH positively stained neurons are smaller in EAE mice than control mice. Representative images from the midcentral portion of the LC of control (FIG. 24A) and EAE mice (FIG. 24B) are shown. The enlarged images show the presence of smaller-sized TH+ stained neurons (asterisks) in EAE (FIG. 24D) but not control (FIG. 24C) mice. Scale bars are 200 µm in FIG. 24A and FIG. 24B; 50 µm in FIG. 24C and FIG. 24D.

Specific staining for the TH+ neurons (FIG. 24) did not reveal any reduction in the number of TH+ stained cells in EAE LC (FIG. 24E); however smaller cells were present in the EAE LC (FIGS. 24C and 24D) and quantitative analysis showed that the average cell body size was significantly reduced in EAE versus control mice (FIG. 24F). Analysis of TH+ cell sizes showed a significant alteration in the frequency distribution between control and EAE mice (FIG. 24G). In control mice most cells (about 60%) were in size bins from 200 to 450 μm$^2$, with fewer cells in the lower and higher bins. In contrast, in EAE mice there were fewer cells in the bin range of 200 to 450 μm$^2$, and an increased percentage of cells in the 2 smallest size bins (between 0 to 100 μm$^2$).

To determine if comparable neuronal damage occurred in multiple sclerosis patients, immunochemical staining of brain samples from 5 multiple sclerosis patients and 6 controls was performed. Immunostaining (FIGS. 18B and 18C) revealed a small non-significant decrease in the average number of TH+ stained cell bodies per section (FIG. 18D). The average cell size (873±33 μm$^2$) in control samples is similar to values reported by others for human LC neurons (German et al., 1988, "The human locus coeruleus: computer reconstruction of cellular distribution," J. Neurosci. 8: 1776-1788), and was significantly increased by approximately 30% in the multiple sclerosis samples (FIG. 18E). This increase was due to a larger percentage of TH+ neurons having cell body areas in the size range of 1,500-2,300 μm$^2$ range (FIG. 18F) and a decrease in the percentage of cells in the smaller range from 700 to 1,100 μm$^2$.

Quantitative PCR of LC RNA Levels

Figure 25:
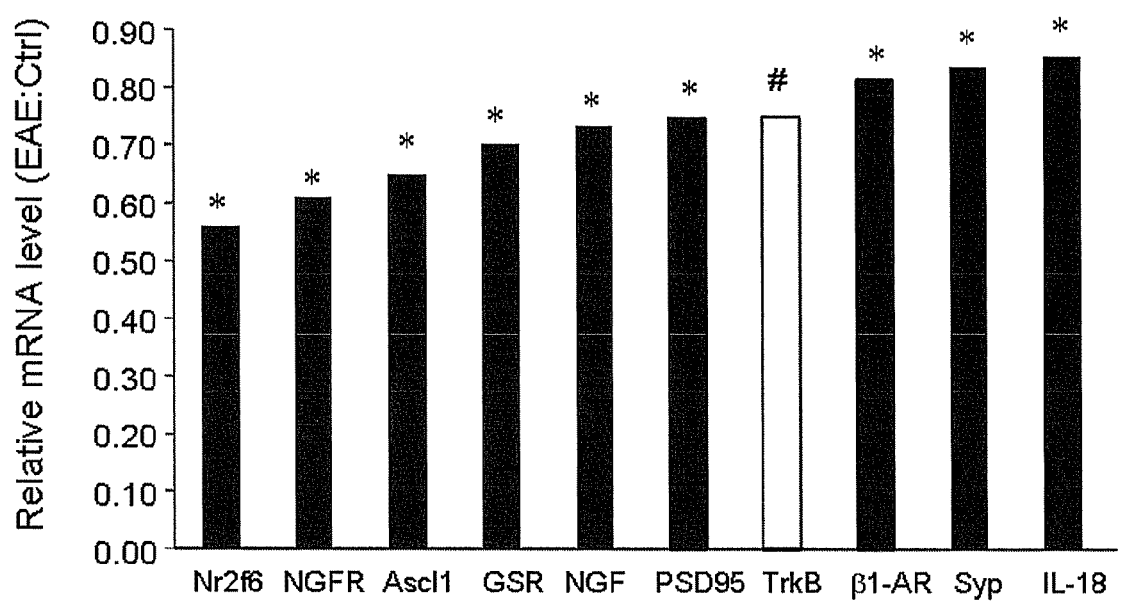
FIG. 25 is a graph showing the ratio of the average level of several mRNA species measured in EAE samples to that measured in control samples, *, P<0.05; EAE versus control. The ratio is shown for the TrkB-receptor which was close to significance (P<0.06). Nr2f6 (Ear2), orphan nuclear receptor subfamily 2 group f member 6; NGFR, p75 nerve growth factor receptor; Ascl1 (Mash1), achaete-scute complex homolog1; GSR, glutathione reductase; NGF, p75 nerve growth factor; PSD95, post-synaptic density protein-95; TrkB, neurotrophic tyrosine kinase receptor, type 2; β1-AR, β1-adrenergic receptor; Syp, synaptophysin; IL-18, interleukin 18.

Quantitative PCR analysis of LC RNA (FIG. 25) revealed several mRNA whose levels were significantly reduced in EAE mice versus controls. This included mRNAs encoding transcription factors Nr2f6 (Ear2) and Ascl1 (Mash1) involved in LC neuronal maturation; the neuronal markers PSD95 and synaptophysin (Syp); the neurotrophin NGF; receptors for NGF and TrkB; the enzyme GSR involved in GSH synthesis; the β1-AR, and pro-inflammatory cytokine IL-18. Interestingly, no significant changes (either reductions or increases) were detected for several mRNAs expected to be reduced due to LC damage, including the LC-enriched genes Phox2a and Phox2B, the catecholamine synthetic enzymes TH or DBH; nor for any of the other adrenergic receptors (β2-AR, β1-AR) measured (Table 2).

TABLE 2

Adrenergic receptors whose mRNA levels remained consistent in EAE mice as compared to controls

| Category | mRNAs |
|---|---|
| House Keeping | b-Act, a-Tub |
| Adrenergic | a1a-AR, b1AR, b2AR, b3AR, Creb1 |
| Amyloid Processing | APP, IDE, NEP, Bace1, Bace2, PSEN1, PSEN2 |
| Neuronal Integrity | NSE, PSD95, Casp3, Syn, Syp |
| Neurotrophins | BDNF, NGF, NGFR, NTN, NT3, TrkB, |
| LC maturation | Bmp5, DBH, Ear2, Mash1, Phox2a, Phox2b, TH |
| Inflammation | CD45, CD11b, IFNg, IL10, IL12p40, IL18, IL4, TNFa |
| PPARs | PPARa, PPARd, PPARg |
| GSH handling | Gpx1, GSR, GSS |

Figure 26:
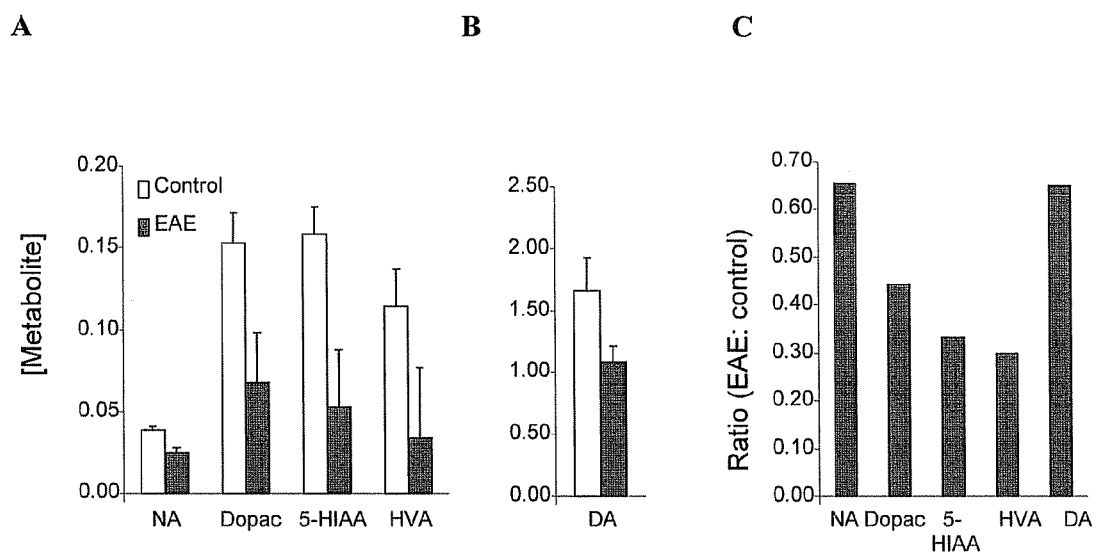
FIG. 26 shows graphs of HPLC analysis of normal and EAE frontal cortex. Extracts obtained by 0.2N perchloric acid extraction were analyzed by HPLC using the frontal cortex of 3 normal mice and 4 EAE mice. Monoamines and their metabolites were analyzed using a SC-20DS HPLC system, EICOM Corp.

HPLC Analysis of EAE and Control Frontal Cortex 0.2N Perchloric acid extracts were obtained from the frontal cortex of 3 normal and 4 EAE mice. Monoamines and their metabolites were analyzed using a SC-20DS HPLC system, EICOM Corp. A reduction of NA and dopamine metabolites as well as a reduction in dopamine was seen in EAE mice (FIG. 26).

Example 13

Effects of NA Reuptake Inhibitor on EAE Mice

To test whether increasing NA derived from the NA precursor L-DOPS in combination with a NA reuptake inhibitor could provide benefit in EAE, C57B16 mice were immunized with MOG$_{35-55}$ peptide using standard procedures as described in Example 9.

Figure 27:
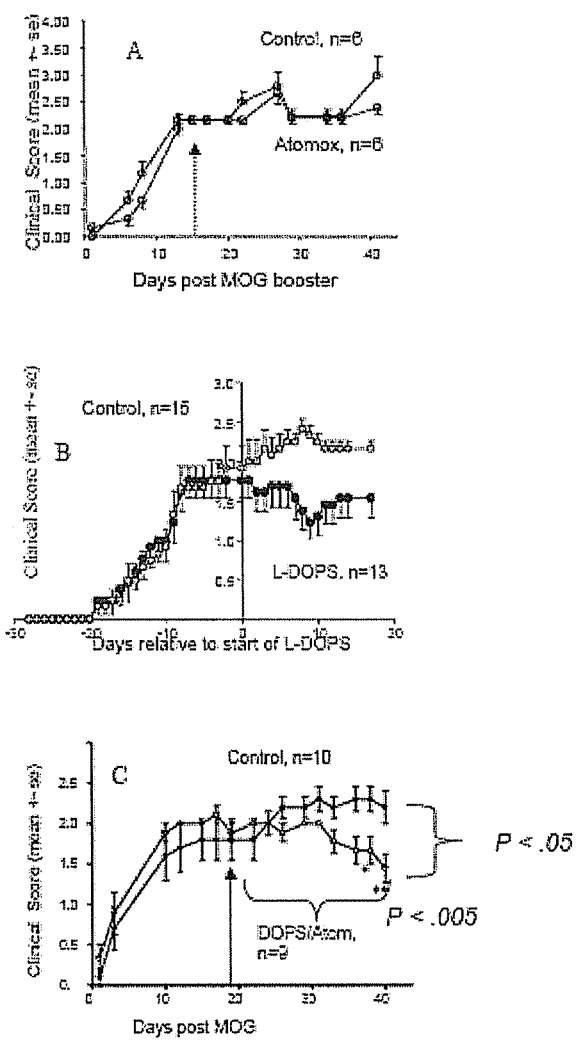
FIGS. 27A through 27C are graphs showing clinical progression of EAE mice after treatment with Axtomoxtine (FIG. 27A), L-DOPS (FIG. 27B) and a combination treatment with Axtomoxtine and L-DOPS (FIG. 27C). p=0.0003, one way ANOVA, *, P<0.05, , P<0.01 vs. first day of treatment (day 17).

To increase brain NA levels starting at day 17 (FIG. 27, arrow) after the booster MOG, 9 EAE mice received triweekly injections of L-DOPS (using a dose of 400 mg/kg s.c.; plus 125 mg/kg bensazeride i.p. to block peripheral conversion to NA) and the non-tricyclic NA selective reuptake inhibitor Atomoxetine (at a dose of 20 mg/kg), and 10 EAE mice received saline. Axtomoxtine administered alone showed limited benefit to ameliorate EAE symptoms. Benefits to EAE were seen when L-DOPS was administered alone, or L-DOPS was coupled with axtomoxtine (FIG. 27). This result showed that increasing NA by co-administration of L-DOPS and Atomoxetine had therapeutic effects at later stages of EAE.

Example 14

COMT Inhibitor and NA Levels

Figure 28:
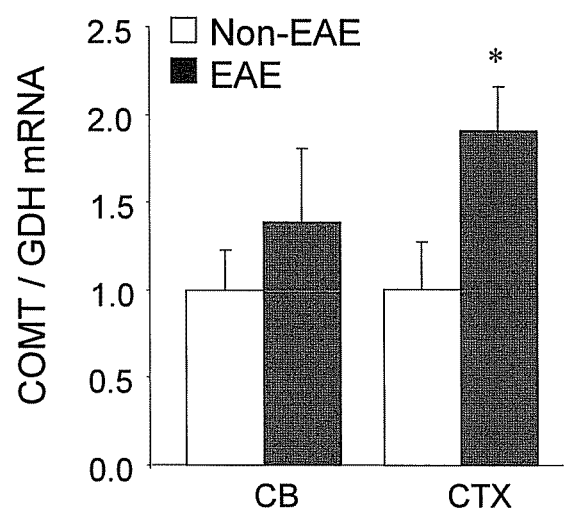
FIG. 28 is a graph showing significantly increased COMT mRNA levels in cerebellum (CB) and frontal cortex of EAE mice as compared to control mice. *, P=0.01.

Levels of COMT were altered in EAE mice compared to control mice. COMT mRNA levels were significantly (P=0.07, n=6) increased in the cerebellum of EAE mice; and significantly (P=0.01) increased in the frontal cortex of the EAE mice compared to controls (FIG. 28). These results suggest that during the progression of EAE (and potentially MS), levels of COMT are increased that would be expected to reduce available levels of NA, as well as increase breakdown of L-DOPS or other NA precursors. These results suggest that inclusion of a COMT inhibitor as a treatment strategy for benefit demyelinating diseases.

Although certain presently preferred embodiments of the application have been described herein, it will be apparent to those of skill in the art to which the application pertains that variations and modifications of the described embodiment may be made without departing from the spirit and scope of the application. Accordingly, it is intended that the application be limited only to the extent required by the following claims and the applicable rules of law.

We claim:

1. A method of slowing progression of a demyelinating disease that is multiple sclerosis or Alzheimer's disease in a mammal comprising the step of administering to a mammal suffering from a demyelinating disease a therapeutically effective amount of an agent that increases noradrenaline levels in the mammal's CNS and a noradrenaline reuptake inhibitor, wherein the agent comprises a noradrenaline precursor that is (−)-threo-3-(3,4-dihydroxyphenyl)-L-serine (L-DOPS) and wherein the reuptake inhibitor that is desipramine, atomoxetine, reboxetine, viloxazine, maprotiline, nortriptyline, bupropion, or radafaxine.

2. The method of claim 1, wherein the agent further comprises at least one of an LAAAD inhibitor and a COMT inhibitor.

3. The method of claim 2, wherein the agent further comprises a COMT inhibitor.

4. The method of claim 3, wherein the COMT inhibitor is (2E)-2-cyano-3-(3,4-dihydroxy-5-nitrophenyl)-N,N-diethylprop-2-enamide(entacapone), 3,4-dinitrocatechol (DNC) or 3-methoxy-L-tyrosine (3MT).

5. The method of claim 4, wherein the COMT inhibitor is entacapone.

6. The method of claim 2, wherein the agent further comprises an LAAAD inhibitor.

7. The method of claim 6, wherein the LAAAD inhibitor is carbidopa or benserazide.

8. The method of claim 7, wherein the LAAAD inhibitor is carbidopa.

9. The method of claim 1, wherein the noradrenaline reuptake inhibitor is atomoxetine.

10. The method of claim 1, wherein the mammal is a human.

* * * * *